United States Patent
Orynbayeva et al.

(10) Patent No.: US 10,253,289 B2
(45) Date of Patent: Apr. 9, 2019

(54) METHOD AND APPARATUS FOR MEASURING BIOLOGICAL ACTIVITY WITH SINGLE CELL RESOLUTION

(71) Applicants: Zulfiya Orynbayeva, Warminster, PA (US); Gennady Friedman, Richboro, PA (US); Yury Gogotsi, Warminster, PA (US); Yang Gao, Philadelphia, PA (US)

(72) Inventors: Zulfiya Orynbayeva, Warminster, PA (US); Gennady Friedman, Richboro, PA (US); Yury Gogotsi, Warminster, PA (US); Yang Gao, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 29 days.

(21) Appl. No.: 15/304,205

(22) PCT Filed: Apr. 17, 2015

(86) PCT No.: PCT/US2015/026311
§ 371 (c)(1),
(2) Date: Oct. 14, 2016

(87) PCT Pub. No.: WO2015/161161
PCT Pub. Date: Oct. 22, 2015

(65) Prior Publication Data
US 2017/0022467 A1    Jan. 26, 2017

Related U.S. Application Data

(60) Provisional application No. 61/980,738, filed on Apr. 17, 2014.

(51) Int. Cl.
| | |
|---|---|
| C12M 1/00 | (2006.01) |
| G01N 33/50 | (2006.01) |
| G01N 33/52 | (2006.01) |
| G01N 33/497 | (2006.01) |
| C12M 1/12 | (2006.01) |
| C12M 1/34 | (2006.01) |
| B01L 3/02 | (2006.01) |

(52) U.S. Cl.
CPC ............ *C12M 29/10* (2013.01); *C12M 23/06* (2013.01); *C12M 41/46* (2013.01); *G01N 33/497* (2013.01); *G01N 33/5005* (2013.01); *G01N 33/5008* (2013.01); *G01N 33/52* (2013.01); *B01L 3/021* (2013.01); *G01N 2033/4975* (2013.01)

(58) Field of Classification Search
CPC .......... G01N 33/5005; G01N 33/5008; G01N 33/52; G01N 33/497; G01N 2033/4975; C12M 29/10; C12M 41/46; C12M 23/06; B01L 3/021
See application file for complete search history.

(56) References Cited

U.S. PATENT DOCUMENTS

8,602,466 B2    12/2013  Barron
2012/0225435 A1    9/2012  Seger et al.

FOREIGN PATENT DOCUMENTS

WO    WO02102404 A2    12/2002

OTHER PUBLICATIONS

Rodolfa, KT et al. Two-component graded deposition of biomolecules with a double-barreled nanopipette. Angew. Chem. Int. Ed. 2005. 44: 6854-6859. (Year: 2005).*
Rodolfa, Kit T., et al. "Nanoscale pipetting for controlled chemistry in small arrayed water droplets using a double-barrel pipet." Nano letters 6.2 (2006): 252-257.
Nashimoto, Yuji, et al. "Isolation and quantification of messenger RNA from tissue models by using a double-barrel carbon probe." Analytical and bioanalytical chemistry 406.1 (2014): 275-282.
Kelbauskas, Laimonas, et al. "Method for physiologic phenotype characterization at the single-cell level in non-interacting and interacting cells." Journal of biomedical optics 17.3 (2012): 0370081-03700812.
Molter, Timothy W., et al. "A microwell array device capable of measuring single-cell oxygen consumption rates." Sensors and Actuators B: Chemical 135.2 (2009): 678-686.
Trimarchi, James R., et al. "Oxidative phosphorylation-dependent and -independent oxygen consumption by individual preimplantation mouse embryos." Biology of reproduction 62.6 (2000): 1866-1874.
Chatni, M. R., and D. M. Porterfield. "Self-referencing optrode technology for non-invasive real-time measurement of biophysical flux and physiological sensing." Analyst 134.11 (2009): 2224-2232.
Osbourn, Damon M., Richard H. Sanger, and Peter JS Smith. "Determination of single-cell oxygen consumption with impedance feedback for control of sample-probe separation." Analytical chemistry 77.21 (2005): 6999-7004.
Taylor, Anne M., et al. "Microfluidic Local Perfusion Chambers for the Visualization and Manipulation of Synapses." Neuron 66 (2010): 57-68.
Gao, D. Y., et al. "Development of a novel microperfusion chamber for determination of cell membrane transport properties." Biophysical journal 71.1 (1996): 443.
Ainla, Alar, et al. "A microfluidic pipette for single-cell pharmacology." Analytical chemistry 82.11 (2010): 4529-4536.
Ainla, Alar, et al. "A multifunctional pipette." Lab Chip 12 (2012): 1255-1261.
Helm, Paul Johannes. "A microscopic setup for combined, and time-coordinated electrophysiological and confocal fluorescence microscopic experiments on neurons in living brain slices." Review of scientific instruments 67.2 (1996): 530-534.

(Continued)

*Primary Examiner* — Renee Claytor
*Assistant Examiner* — Susan E. Fernandez
(74) *Attorney, Agent, or Firm* — Mendelsohn Dunleavy, P.C.

(57) ABSTRACT

A method and apparatus for carrying out measurements on single cells, either one or many single cells at a time in order to characterize the cellular response to stimuli in a perfused liquid. The apparatus for performing the respirometry includes a double-barrel pipette probe.

16 Claims, 17 Drawing Sheets

(56) References Cited

OTHER PUBLICATIONS

Ferrea, Enrico, et al. "Large-scale, high-resolution electrophysiological imaging of field potentials in brain slices with microelectronic multielectrode arrays." Frontiers in neural circuits 6 (2012): 80.

Zhao, C., et al., Effect of Film Thickness on the Antifouling Performance of Poly(hydroxy-functional methacrylates) Grafted Surfaces. Langmuir, 2011. 27(8): p. 4906-4913.

Yellen, B.B. and G. Friedman, Programmable assembly of colloidal particles using magnetic microwell templates. Langmuir, 2004. 20(7): p. 2553-9.

Singhal, R., et al., Small diameter carbon nanopipettes. Nanotechnology, 2010. 21(1): p. 015304.

International Search Report and Written Opinion; dated Jun. 18, 2015 for PCT Application No. PCT/US15/26311.

Pollard, Andrew J., et al. "Development of a novel combined scanning electrochemical microscope (SECM) and scanning ion-conductance microscope (SICM) probe for soft sample imaging." MRS Proceeding. vol. 1422. Cambridge University Press, 2012.

Gao, Y., et al. "Perfusion Double-Channel Mirco-Pipette Probes for Oxygen Flux Mapping with Single Cell Resolution," Lab Chip, 2015, 00, 1-6, pp. 1-9.

\* cited by examiner

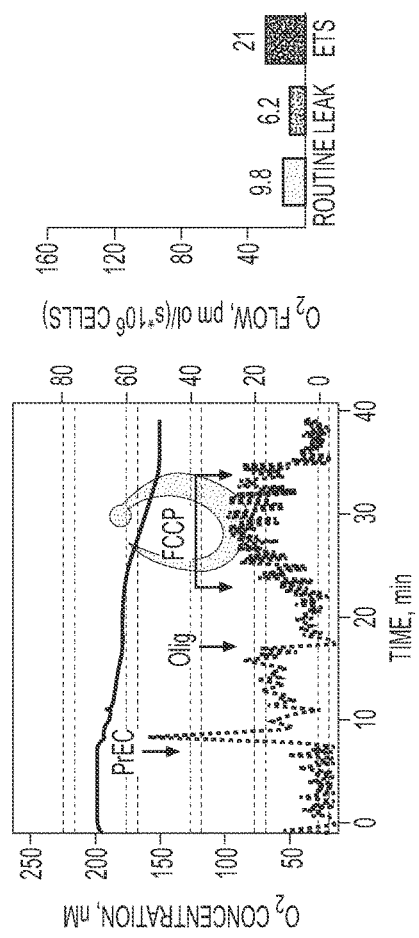
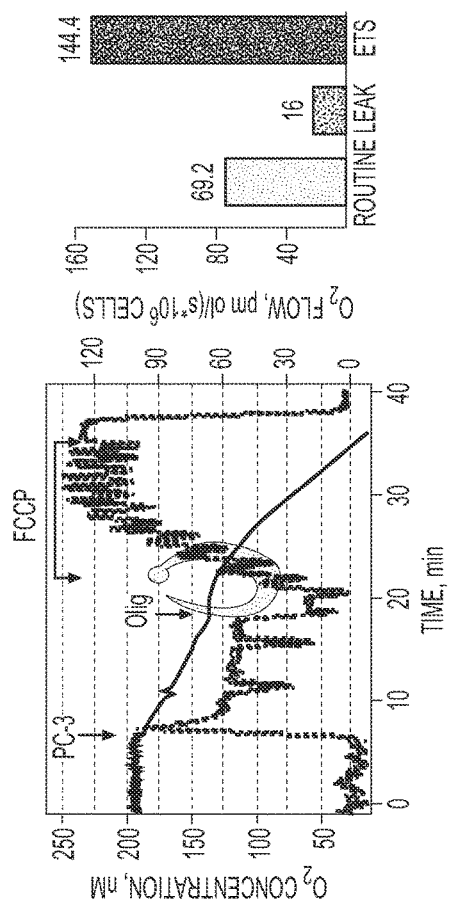
FIG. 2A
FIG. 2B

US 10,253,289 B2

METHOD AND APPARATUS FOR MEASURING BIOLOGICAL ACTIVITY WITH SINGLE CELL RESOLUTION

This application claims the benefit of U.S. Provisional Application Ser. No. 61/980,738, the contents of which are incorporated herein by reference.

BACKGROUND OF THE INVENTION

Field of Invention

The present invention is directed to the field of biological analysis. In particular the field of the invention is directed to measuring biological activity at a cellular level.

Description of the Related Technology

The fundamental limitation of the currently available technology is that it requires many thousands of cells in the cell culture or tissue to produce sufficient signal of oxygen or glucose consumption, exchange of ions such as sodium and potassium, release of molecules such as lactic acid or other signals related to cell functionality. The resulting measurements provide information about cellular function averaged over a relatively large cell population. However, most cell populations have large heterogeneity of cellular behaviors and functions, even within genetically identical populations. Some cells being of a different phenotype may respond differently to external stimuli, for example, consuming oxygen at dramatically different rates than others. Such heterogeneity is an important property of many tissues and disease types.

The only known methodology for single cell function measurements such as respirometry is based on housing the cell being examined in a sealed micro-chamber. The main shortcomings of this scaled micro-chamber approach is that the relatively rapid depletion of essential molecules such as oxygen or nutrients as well as accumulation of carbon dioxide has the potential to change the observed cell behavior over time. Sealed chamber measurements must be carried out sufficiently quickly, usually faster than within few minutes, making it impossible to study cell behavior over longer time periods. Furthermore, sealed chamber approach to respirometry does not permit injection of molecules that can modify various aspects of cellular metabolism.

SUMMARY OF THE INVENTION

In an aspect of the present invention is a double barrel pipette probe system for perfusing a single cell with a liquid and measuring the single cell's effect on the liquid, said system comprising a double barrel pipette probe (1), a capillary tube (20) connecting channel A (6) to a fluid pump (21) and a capillary tube (20) connecting channel B (7) to the fluid pump (21), said double barrel pipette probe (1) comprising a pipette shaft body (2) having a distal end (5), wherein the pipette shaft body (2) comprises two channels A (6) and B (7), wherein channel A (6) is configured for flow of liquid out of the distal end of the tip and channel B (7) is configured to receive the flow of liquid exiting channel A (6) at the distal end (5) of the pipette shaft body (2), wherein said channel B (7) comprises or is in fluid connection with a sensor module for measuring a concentration of material in the liquid or a temperature of the liquid.

In another aspect of the invention is a method of perfusing a single cell with a liquid and measuring the single cell's effect on the liquid using a double barrel pipette probe (1) comprising a pipette shaft body (2) having a distal end (5), wherein the pipette shaft body (2) comprises two channels A (6) and B (7), wherein channel A (6) is configured for flow of liquid out of the distal end of the tip and channel B (7) is configured to receive the flow of liquid exiting channel A (6) at the distal end (5) of the pipette shaft body (2), wherein said channel B (7) comprises or is in fluid connection with a sensor module for measuring a concentration of material in the liquid or a temperature of the liquid, said method comprising positioning said distal end (5) in proximity to said single cell, maintaining flow of the liquid from channel A (6) having a baseline concentration of material or baseline temperature to channel B (7) at the distal end (5) while perfusing said single cell with the liquid exiting channel A (6), and measuring the concentration of the material in the liquid or temperature of the liquid with the sensor module in channel B (7), and comparing the baseline concentration of material or baseline temperature with the concentration of material or the temperature of the liquid as measured by the sensor module, to determine an effect of said single cell.

BRIEF DESCRIPTION OF THE DRAWINGS

FIG. 2 shows a study of prostate cancer metabolism using an Oxygraph-2K respirometer.

CERTAIN ASPECTS OF THE INVENTION

Method Of Use

Figure 1:
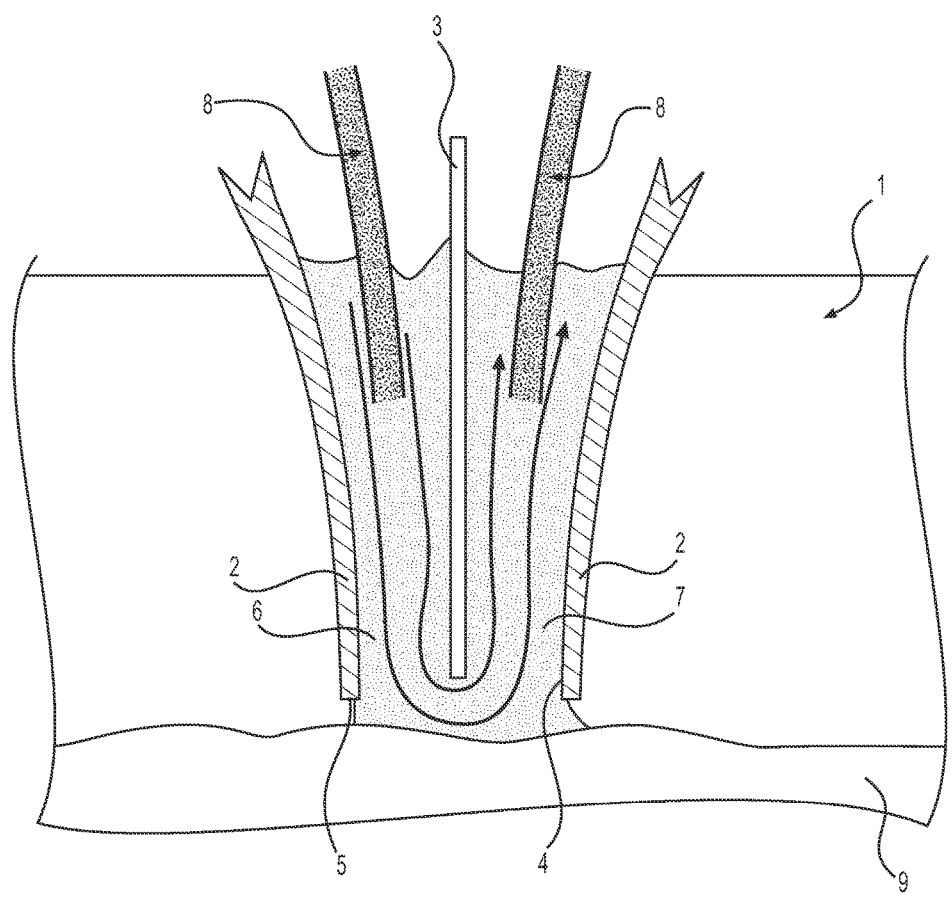
FIG. 1 shows the inventive double-barrel pipette probe when used as a respirometer.

1. A method of perfusing a single cell with a liquid and measuring the single cell's effect on the liquid using a double barrel pipette probe (1) comprising a pipette shaft body (2) having a distal end (5), wherein the pipette shaft body (2) comprises two channels A (6) and B (7), wherein channel A (6) is configured for flow of liquid out of the distal end (5) of the pipette shaft body (2) and channel B (7) is configured to receive the flow of liquid exiting channel A (6) at the distal end (5) of the pipette shaft body (2), wherein said channel B (7) comprises or is in fluid connection with the sensor module for measuring a concentration of material in the liquid or a temperature of the liquid, said method comprising positioning said distal end (5) of the pipette shaft body (2) in proximity to said single cell, maintaining flow of the liquid from channel A (6) having a baseline concentration of material or baseline temperature to channel B (7) at the distal end (5) while perfusing said single cell with the liquid exiting channel A (6), and measuring the concentration of the material in the liquid or the temperature of the liquid with the sensor module in channel B (7), comparing the baseline concentration of material or baseline temperature with the concentration of material or the temperature of the liquid as measured by the sensor module to determine an effect of said single cell.

2. The method of item 1, wherein a separator wall (3) connects opposite sides of an inner wall (4) of the pipette shaft body (2), said separator wall (3) is formed in a plane bisecting a lumen of the pipette shaft body (2) in a longitudinal direction, whereby said separator wall (3) separates the pipette shaft body (2) into said two channels A (6) and B (7), channel A (6) is parallel to channel B (7) and the direction of flow of liquid within channel A (6) is opposite a direction of flow of liquid within channel B (7).

3. The method of item 1 or 2, wherein said two channels A (6) and B (7) are coaxial and the pipette shaft body (2) is an outer tube encompassing an inner tube, wherein a space between the outer tube and the inner tube is one of channel A or channel B, and a lumen of the inner tube is the other of channel A or channel B, there is optionally at least one spacer which maintains the distance between the outer tube and the inner tube, and a direction of flow of liquid within channel A (6) is opposite a direction of flow of liquid within channel B (7).

4. The method of any one of items 1-3, wherein the pipette shaft body (2) has a conical tip portion narrowing at the distal end (5) and the distal end (5) of the conical tip portion has a diameter of from about 100 nm to about 100 microns.

5. The method of any one of items 1-4, wherein the single cell is one cell in a tissue sample (9) containing other cells.

6. The method of any one of items 1-5, wherein the material comprises oxygen and the liquid further comprises a respiration modulator.

7. The method of item 6, wherein the respiration modulator is at least one selected from the group consisting of a metabolite, mitochondrial electron transport inhibitor, chemotherapeutic agent, and a compound which affects extracellular pH.

8. The method of any one of items 1-7, wherein the material is at least one of oxygen, alkali metal cation, an alkaline earth metal cation and a halide.

9. The method of any one of items 1-8, wherein the single cell is perfused for at least 10 minutes, preferably at least 20 minutes, and if necessary up to many (e.g. 24) hours.

10. The method of item 5, wherein the double barrel pipette probe is a first pipette probe and said method further comprises perfusing second single cell with a liquid using a second double barrel pipette probe in proximity to a second single cell in the tissue sample, determining a baseline of a material in the liquid in channel B of the second pipette probe, adding a modulator to the liquid in channel A of the first pipette probe, and measuring for variations in the liquid in channel B of the second pipette probe.

11. The method of any one of items 1-10, wherein channel A (6) comprises a sensor module.

12. The method of any one of items 1-11, wherein the cell is an animal cell.

13. The method of any one of items 1-12, wherein the cell is isolated in a well (30).

14. The method of any one of items 1-13, wherein a wall of channel B (7) and a wall of channel A (6) have a carbon coating.

15. The method of any one of items 1-14, wherein the sensor module is a coating (41) capable of providing a fluorescent response in the presence of at least one of glucose, lactose, protein, carbon dioxide, sodium, chlorine, potassium, iron, magnesium and calcium.

16. The method of item 15, wherein a microscope objective (42) is positioned below a substrate (43) holding the single cell or tissue so as to receive a light signal through the substrate.

17. The method of any one of items 1-16, wherein the sensor module is an oxygen sensor (8) or a plasma discharge wire (50).

18. The method of any one of items 1-17, wherein the diameter of the channels A and B at the distal end (5) of the pipette shaft body (2) is reduced by occlusions affixed to walls of channel A and channel B.

19. The method of item 16, wherein the distance from the distal end (5) of the pipette shaft body (2) to the substrate (43) is less than 20 microns, preferably less than 10 microns, most preferably ≤5 microns.

20. The method of any one of items 1-19, wherein the single cell is within 20 microns of an imaginary line extending along longitudinal axis at a center of the pipette shaft body (2), preferably, within 5 microns, most preferably said imaginary line also runs through the single cell.

21. The method of any one of items 1-20, wherein the sensor module is positioned up to 2 mm from the distal end (5) of the pipette shaft body (2), optionally 100 microns to 2 mm from the distal end (5) of the pipette shaft body (2), or 150 microns to 2 mm from the distal end (5) of the pipette shaft body (2).

22. The method of any one of items 1-21, wherein the distal end (5) of the pipette shaft body (2) has a diameter which is no more than 5 microns greater than the diameter of the single cell or the maximum diameter of a single cell in a tissue sample (9), preferably no more than 1 micron greater than the diameter of the single cell or the maximum diameter of a single cell in a tissue sample (9), more preferably the distal end (5) has a diameter which ±100 nm of the diameter of the single cell or the maximum diameter of a single cell in a tissue sample (9).

23. The method of any one of items 1-22, wherein single cells are isolated in an array of wells (61) or are surface cells of a tissue sample, and more than two double barrel pipette probes (60) are each used to perfuse different single cells, and a difference in concentration or temperature values effected by each single cell is measured and collected.

24. The method of any one of items 1-23, wherein the distal end (5) of the pipette shaft body (2) has a conical tip portion having a half-angle of less than 45°, preferably, 5 to 30°, more preferably 5 to 20°.

25. The method of any one of items 1-24, further comprising introducing material into the fluid travelling towards channel A through a capillary tube (20) in a controlled manner with an infusion pump (25).

26. The method of any one of items 1-25, further comprising monitoring the pressure of the fluid in channel A (6) and channel B (7) with a component (23) and obtaining desired flow of liquid by increasing or decreasing the pressure of the liquid in channel A (6) and channel B (7) with a fluid pump (21).

27. The method of item 3, wherein a single cell on the surface of the tissue is exposed to a modulator at a baseline concentration and/or duration and the depth of response within the tissue cells is measured, then the single cell on the surface of the tissue is exposed to a modulator at an increased concentration and/or duration and the depth of response within the tissue cells is measured.

Double Barrel Pipette Probe

1'. A double barrel pipette probe (1) for use in perfusing a single cell with a liquid and measuring the single cell's effect on the liquid, said double barrel pipette probe comprising;
a pipette shaft body (2) having a separator wall (3) connecting opposite sides of an inner wall (4) of the pipette shaft body (2), wherein said separator wall (3) is formed in a plane bisecting a lumen of the pipette shaft body (2) in a longitudinal direction, wherein the pipette shaft body (2) has a conical tip portion narrowing at a distal end (5) and the distal end (5) has a diameter of from about 100 nm to about 100 microns, wherein said separator wall (3) separates the pipette shaft body (2) into two channels A (6) and B (7), channel A (6) is configured for flow of liquid out of the distal end (5) of the tip, channel B(7) is configured to receive the flow of liquid exiting channel A (6) at the distal end (5) of the tip, said channel B (7) comprises or is in fluid connection with a sensor module for measuring a concentration of material in the liquid or a temperature of the liquid, wherein channel A (6) is parallel to channel B (7) and channel A (6) is on an opposite side of the separator wall (3) from channel B (7).

2'. A double barrel pipette probe (1) for use in perfusing a single cell with a liquid and measuring the single cell's effect on the liquid, said double barrel pipette probe comprising: a pipette shaft body (2) having a distal end (5), wherein the pipette shaft body (2) comprises two channels A (6) and B (7), wherein channel A (6) is configured for flow of liquid out of the distal end (5) of the pipette shaft body (2), channel B (7) is configured to receive the flow of liquid exiting channel A (6) at the distal end (5) of the pipette shaft body (2), said channel B (7) comprises or is in fluid connection with the sensor module for measuring a concentration of material in the liquid or a temperature of the liquid, said two channels A (6) and B (7) are coaxial and the pipette shaft body (2) is an outer tube encompassing an inner tube, a space between the outer tube and the inner tube is one of channel A or channel B, and a lumen of the inner tube is the other of channel A or channel B, the distal end (5) of the pipette shaft body (2) has a cross section which is generally in the shape of the letter O in a circle, and there is optionally at least one spacer which maintains a distance between the outer tube and the inner tube, the pipette shaft body (2) has a conical tip portion narrowing at a distal end (5) having a cross section substantially in a shape of the Greek letter O when viewed from below the pipette shaft body (2) and the distal end (5) has a diameter of from about 100 nm to about 100 microns.

3'. The pipette probe according to item 1' or 2', further comprising a sensor module in channel A or in fluid connection with channel A.

4'. The pipette probe according to any one of items 1'-3', further comprising a coating (41) on the inner wall (4) of the pipette shaft body (2).

5'. The pipette probe according to any one of items 1'-4', wherein the pipette shaft body (2) is made of glass.

6'. The pipette probe according to any one of items 1'-5', wherein a wall of channel B (7) and a wall of channel A (6) have a carbon coating.

7'. The pipette probe according to any one of items 1'-6', wherein the sensor module is a coating (41) capable of providing a fluorescent response in the presence of at least one of glucose, lactose, protein, carbon dioxide, sodium, chlorine, potassium, iron, magnesium and calcium.

8'. The pipette probe according to item 7', wherein a microscope objective (42) is positioned below a substrate (43) holding the single cell or tissue.

9'. The pipette probe according to any one of items 1'-8', wherein the sensor module is an oxygen sensor (8) or a plasma discharge wire (50).

10'. The pipette probe according to any one of items 1'-9', wherein the diameter of a lumen of the distal end (5) of the tip is reduced by occlusions affixed to walls of channel A and channel B.

11'. The pipette probe of any one of items 1'-10', wherein the conical tip portion has a half-angle of less than 45°, preferably, 5 to 30°, more preferably 5 to 20°.

Double Barrel Pipette Probe System

1". A double barrel pipette probe system for perfusing a single cell with a liquid and measuring the single cell's effect on the liquid, said system comprising a double barrel pipette probe (1), a capillary tube (20) connecting a channel A (6) to a fluid pump (21) and a capillary tube (20) connecting a channel B (7) to the fluid pump (21), said double barrel pipette probe (1) comprising a pipette shaft body (2) having a distal end (5) wherein the pipette shaft body (2) comprises the two channels A (6) and B (7), wherein channel A (6) is configured for flow of liquid out of the distal end of the pipette shaft body (2) and channel B (7) is configured to receive the flow of liquid exiting channel A (6) at the distal end (5) of the pipette shaft body (2), wherein said channel B (7) comprises or is in fluid connection with the sensor module for measuring concentration of material in the liquid or temperature of the liquid.

2". The pipette probe system according to item 1", wherein a separator wall (3) connects opposite sides of an inner wall (4) of the pipette shaft body (2), said separator wall (3) is formed in a plane bisecting a lumen of the pipette shaft body (2) in a longitudinal direction, the distal end (5) of the pipette shaft body (2) has a cross section in the shape of the Greek letter θ when viewed from below the pipette shaft body (2), said separator wall (3) separates the pipette shaft body (2) into said two channels A (6) and B (7), and channel A (6) is parallel to channel B (7).

3". The pipette probe system of item 1" or 2", wherein said two channels A (6) and B (7) are coaxial and the pipette shaft body (2) is an outer tube encompassing an inner tube, a space between the outer tube and the inner tube is one of channel A or channel B, and a lumen of the inner tube is the other of channel A or channel B, the distal end (5) of the pipette shaft body (2) has a cross section which is generally in the shape of the letter O in a circle, and there is optionally at least one spacer which maintains the distance between the outer tube and the inner tube.

4". The pipette probe system of any one of items 1"-3", wherein the pipette shaft body (2) has a conical tip portion narrowing at the distal end (5) and the distal end (5) has a diameter of from about 100 nm to about 100 microns.

5". The pipette probe system of claim 1", further comprising an infusion pump (25) for introducing material into the fluid travelling towards channel A through a capillary tube (20) in a controlled manner.

6". The pipette probe system of claim 1", wherein a component (23) for measuring pressure of liquid is in fluid connection directly or indirectly to channel A (6) and channel B (7) so as to be able to measure the pressure of fluid in channel A (6) and channel B (7).

7". The pipette probe system of claim 1", further comprising a motorized computer controlled stage (22) for holding a single cell or a tissue sample and which can move in one or more directions so as to maintain a desired position of the single cell or cells in the tissue sample with respect to the distal end of the pipette shaft body (2).

8". The pipette probe system of claim 1", further comprising piezoelectric controlled pipette manipulators and a stage for holding a single cell or a tissue sample, wherein the manipulators grip the pipette and are capable of moving the pipette in one or more directions so as to maintain a desired position of the single cell or cells in the tissue sample with respect to the distal end of the pipette body (2).

9". The pipette probe system of claim 1", wherein the double barrel pipette probe is a first pipette probe and said system further comprises a second double barrel pipette probe in proximity to a second single cell in the tissue sample for perfusing the second single cell with a liquid using the second pipette probe, means for determining a baseline of a material in the liquid in channel B of the second pipette probe and for measuring variations in the liquid in channel B of the second pipette probe after a modulator is added to the liquid in channel A of the first pipette probe.

10". The pipette probe system of claim 1", wherein a wall of channel B (7) and a wall of channel A (6) have a carbon coating.

11". The pipette probe system of claim 10", wherein the sensor module is a coating (41) capable of providing a fluorescent response in the presence of at least one of glucose, lactose, protein, carbon dioxide, sodium, chlorine, potassium, iron, magnesium and calcium.

12". The pipette probe system of claim 1", wherein a microscope objective (42) is positioned below a substrate (43) holding the single cell or tissue so as to be capable of receiving a signal through the substrate.

13". The pipette probe system according to claim 1", wherein the sensor module is an oxygen sensor (8) or a plasma discharge wire (50).

14". The pipette probe system according to claim 1", wherein the diameter of a lumen of the distal end (5) of the tip is reduced by occlusions affixed to walls of channel A and channel B.

15". The pipette probe system of claim 1", wherein the distance from distal end (5) of the tip to the substrate (43) is less than 20 microns, preferably less than 10 microns, most preferably ≤5 microns.

16". The pipette probe system of claim 1", wherein the sensor module is positioned up to 2 mm from the distal end (5) of the tip, optionally 100 microns to 2 mm from the distal end (5) of the tip, or 150 microns to 2 mm from the distal end (5) of the tip.

17". The pipette probe system of claim 1", wherein more than two double barrel pipette probes (60) are positioned so as to be capable of perfusing different single cells in an array of wells (61) or different single cells in a surface of a tissue sample.

18". The pipette probe system of claim 2", wherein the conical tip portion has a half-angle of up to 45°, preferably 5 to 30°, more preferably 5 to 20°.

DETAILED DESCRIPTION OF THE PREFERRED EMBODIMENT(S)

For illustrative purposes, the principles of the present disclosure are described by referencing various exemplary embodiments. Although certain embodiments are specifically described herein, one of ordinary skill in the art will readily recognize that the same principles are equally applicable to, and can be employed in other systems and methods.

Before explaining the disclosed embodiments of the present disclosure in detail, it is to be understood that the disclosure is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel methods are therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

An aspect of the invention relates to biological measurements known as respirometry. Respirometry is essentially based on measurement of oxygen consumption in the fluid medium surrounding cells or tissues, while adding various molecules that could modify oxygen consumption of cells or tissues. Comparison of oxygen consumption rates for different cells and tissues as well as for the same cells and tissues in the presence of different molecular species in the extracellular fluid or inside the cells provides the ability to make conclusions regarding the mechanism of cellular respiration, mitochondrial activity or pathology within cells and tissues and, more generally, regarding metabolic dysfunctions relevant in many diseases including cancer and neurological diseases.

Respirometers can generally be classified as biological instruments capable of quantifying mitochondrial respiration processes and playing an important role in cellular physiology studies. Compromised mitochondrial status is implicated in a wide range of pathologies, including cancer, neurodegeneration, diabetes, inflammation, and aging. Respirometry has been shown to provide information about defects in mitochondrial membrane structure, of respiratory and transport enzymes, dehydrogenases, electron transport and coupled ATP production.

Classical respirometry is based on measurements of oxygen in solution using Clark electrodes. Modern alternatives can also employ fluorescence-based measurements via optical fibers. Dominant among today's high-resolution respirometers are those offered by SEAHORSE (XF Analyzer) and OROBOROS (Oxygraph-2K). These devices are capable of using relatively small biological samples containing several thousand to few millions of cells, correspondingly. An example of respirometry data in the study of prostate cancer using OROBOROS Oxygraph-2K are shown in FIG. 2.

In FIG. 2, the oxygen concentration vs. time for human prostate benign PrEC (Graph A) and cancer PC-3 cells (Graph B) are shown in the darker line that is relatively straight, while lighter colored traces are calculated oxygen consumption rates. ATP-synthase inhibitor Oligomycin and uncoupler of oxidative phosphorylation FCCP (carbonyl cyanide 4-(trifluoromethoxy)phenylhydrazone) are added to study proton leakage (Leak) and electron transport maximum capacity (ETS). The bar graphs show oxygen consumption rates at rest (Routine) and after addition of the modulators. The data clearly indicates much higher respiration capacity of the cancer cells.

These comparative studies of metabolism in normal and metastatic cells of human prostate have revealed that the normal cells have very low respiratory rates, while prostate metastatic cells acquire almost 10 times higher respiration activities (69.2 versus 9.8 pmol*s$^{-1}$ per $10^6$ cells of routine, unstimulated respiration). Cancer cells are also characterized by very high maximal capacity of their mitochondria (144.4 versus 21 pmol*s$^{-1}$ per $10^6$ cells of ETS respiration). The respiratory analysis clearly indicates dramatic differences in energetic activities of prostate normal and cancer cells, wherein partly oxidative capacity for ATP production is a necessary condition for increased mitochondria membrane potential, which reduces the probability of mitochondria permeability transition pore opening and helps highly metastatic cancer cells escape the apoptotic cell death.

However, conventional techniques which give data based on an average from a large number of cells often misses potential cell differences that help them survive adverse conditions (like chemotherapy or radiation treatment). Recent studies of single cell genomics and proteomics indicate significant heterogeneity of cells within a population. It is evident that averaged characteristics recorded from a relatively large population can obscure important differences. Having only gene and protein profiling of individual cells would provide little meaning unless these data are accompanied by evaluation of the functional activity, with cell respiration activity being among the most critical cell functions. For this reason, development of a viable single cell respirometer such as the inventive double barrel pipette probe system can play a critical role in the growing area of single cell analysis.

A few decades ago, there were several attempts to design microelectrodes for respiration measurements based on the principles of the conventional oxygen Clark electrode and also to operate microchambers. However, their applications were restricted or were problematic for certain reasons, including declined electrode stability with the reduction of cathode area, or unsuitable vessel design. Several reports of single cell oxygen consumption measurements have appeared in recent years. All of them seem to fall into two categories: 1) measurement on isolated cells sealed within substrate micro-wells and 2) scanning microprobe based measurements. Optical (such as those based on oxygen induced fluorescence or luminescence lifetime) and electrochemical oxygen sensing have been employed in both types of devices. The main shortcomings of micro-well and scanning probe-based approaches are not due to oxygen sensing difficulties, however. Microprobes, although attractive due to the possibility of working with tissues, provide no means for isolating cellular sources of oxygen diffusing toward the probe and require accurate positioning or source estimation tactics. Sealed micro-wells, on the other hand, provide a small and fixed amount of nutrients and oxygen that get depleted over time. Accumulation of carbon dioxide within the micro-wells also changes the cellular environment over time making it difficult to provide clear biological interpretation to the oxygen consumption data. This constraint also limits the utility of the technique for longer-term physiological studies. Increasing the micro-well volume does not seem to be a good option because it reduces the relative change in oxygen measurement. Furthermore, currently available commercial cell culture sized respirometers offer the possibility to inject various molecules into the fluid in order to modify cellular behavior. In addition, stimulation at different times is not possible, however, with sealed micro-well respirometry. On the other hand, the inventive double barrel pipette probe system allows for application of various mitochondrial substrates, inhibitors, and uncouplers, with stepwise evaluation of the functional activity of respiratory enzymes in real-time using measured oxygen consumption rates of individual cells, using the same protocol as illustrated in FIG. 2 for biological samples of a few million cells with OROBOROS Oxygraph-2k.

Double Barrel Pipette Probe

As illustrated in the embodiment of FIG. 1, an aspect of the invention is a double barrel pipette probe (1) for use in perfusing a single cell with a liquid and measuring the single cell's effect on the liquid, said double barrel pipette probe comprising a pipette shaft body (2) having a distal end (5), wherein the pipette shaft body (2) comprises two channels A (6) and B (7), wherein channel A (6) is configured for flow of liquid out of the distal end of the tip and channel B (7) is configured to receive the flow of liquid exiting channel A (6) at the distal end (5) of the tip, wherein said channel B (7) comprises a sensor module or is in fluid connection with the sensor module for measuring concentration of material in the liquid or temperature of the liquid, wherein the pipette shaft body (2) has a conical tip portion narrowing at a distal end (5), wherein the distal end (5) has a diameter of from about 100 nm to about 100 microns.

In an embodiment, a separator wall (3) connects opposite sides of an inner wall (4) of the pipette shaft body (2), wherein said separator wall (3) is formed in a plane bisecting a lumen of the pipette shaft body (2) in a longitudinal direction, wherein the distal end (5) of the pipette shaft body (2) has a cross section in the shape of the Greek letter theta when viewed from below the pipette shaft body (2), wherein said separator wall (3) separates the pipette shaft body (2) into said two channels A (6) and B (7), wherein channel A (6) is parallel to channel B (7).

In another embodiment, the two channels A (6) and B (7) are coaxial and the pipette shaft body (2) is an outer tube encompassing an inner tube, wherein a space between the outer tube and the inner tube is one of channel A (6) or channel B (7), and a space in the inner tube is the other of channel A (6) or channel B (7), wherein the distal end (5) of the pipette shaft body (2) has a cross section which is generally in the shape of the letter O in a circle, wherein there is optionally at least one spacer which maintains the distance between the outer tube and the inner tube, wherein the direction of flow of liquid within channel A (6) is opposite the flow of liquid within channel B (7). The spacer is designed to maintain the distance between the outer tube and the inner tube and keep the outer tube and the inner tube parallel to one another. The spacer could be a wire or thin wall (made of plastic, metal or glass), and is preferably designed to have minimal influence on the flow of liquid through the channel.

The sensor module is part of a sensing system that is in contact with the liquid during operation, and the sensor module is used for measuring concentration or presence of material in the liquid or temperature of the liquid used in perfusion. In one aspect, the sensor module is a thermocouple. In another aspect, the sensor module is a coating (41) capable of providing a fluorescent response in the presence of at least one of glucose, lactose, protein, carbon dioxide, sodium, chlorine, potassium, iron, magnesium and calcium. The fluorescent light is measured with a fluorescence measuring device containing a microscope objective (42) which is positioned below a substrate (43) holding the single cell or a tissue sample (9). See for example, FIG. 12. In addition to, or in the alternative, a microscope objective (42) can be positioned to the side of the substrate (43) and the tip of the probe. Measurement of fluorescent lifetime have been observed to yield good sensitivity.

Figure 13:
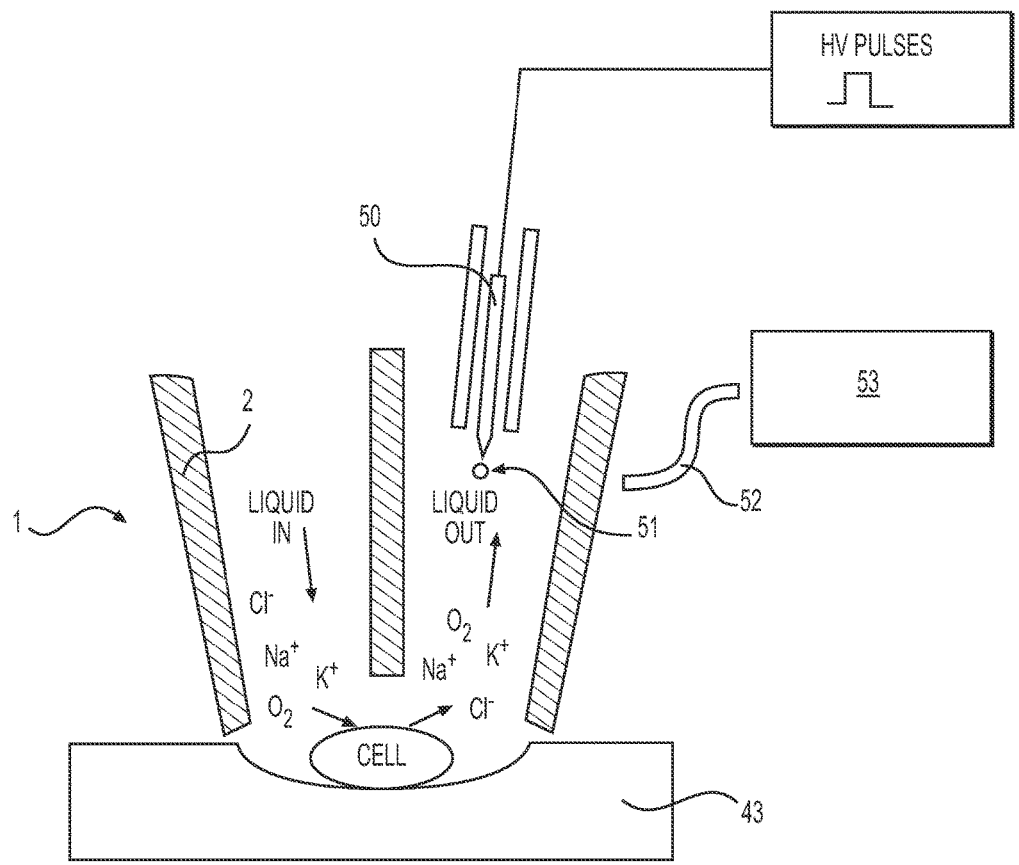
FIG. 13 shows an illustration of the double barrel pipette probe used as a respirometer that includes ion concentration (focusing primarily on sodium, potassium and chloride) measurement that determines cell's ion exchange with the surrounding liquid.
Figure 14A:
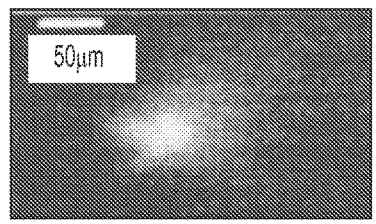
FIG. 14 shows optical emission spectra (OES) and corona discharges produced using 5 kV stepped and pulsed voltage (duration from 20 ns to several microseconds) excitation in liquids using tungsten wire with tips below 200 nm.
Figure 14B:
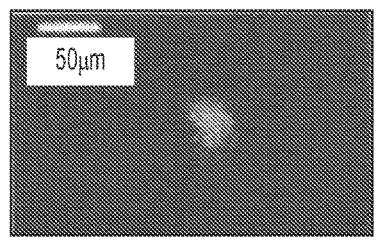
Figure 14C:
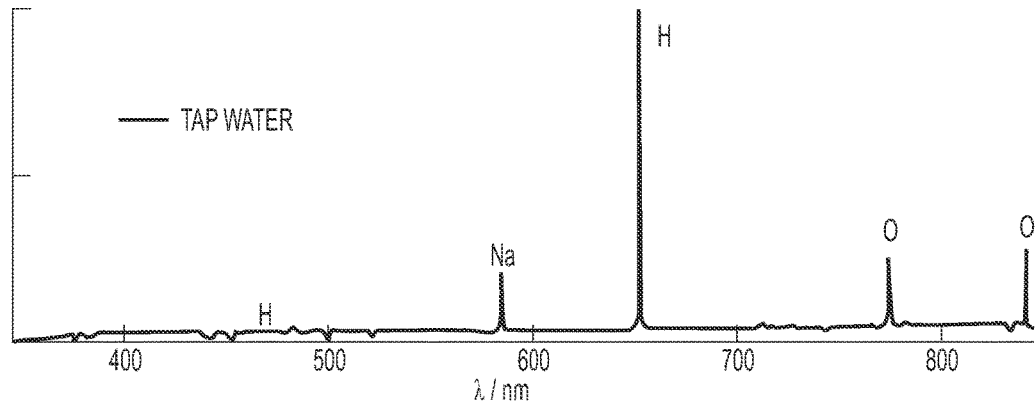
Figure 14D:
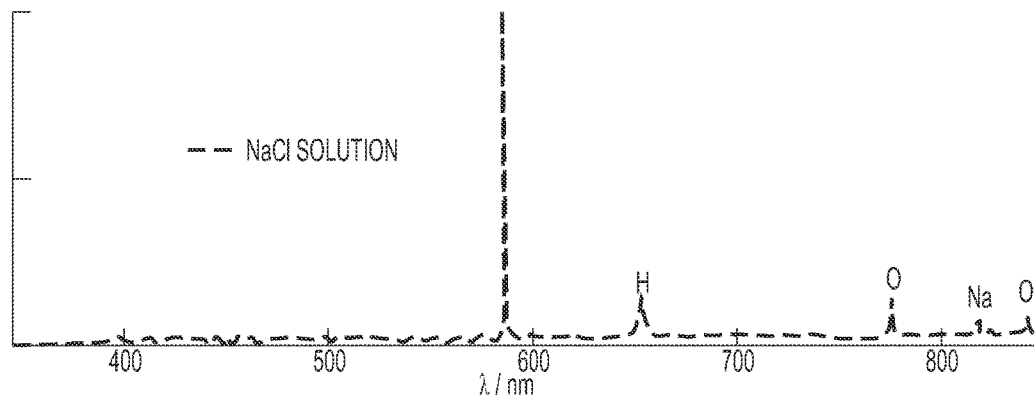
Figure 14E:
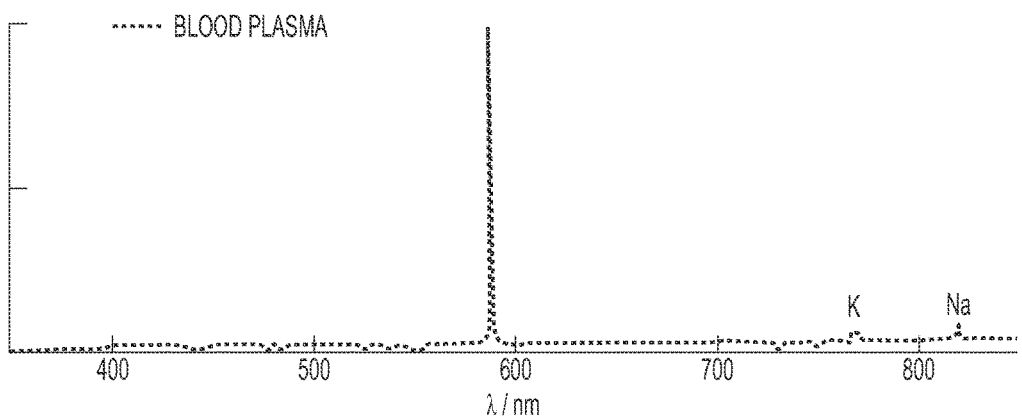
Figure 14F:
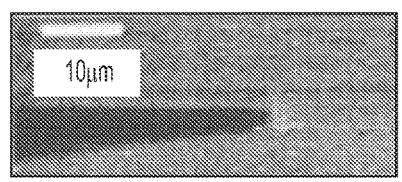
Figure 14G:
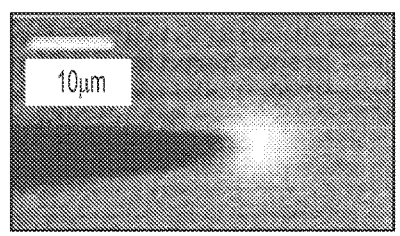

In another aspect, the sensor module is an oxygen sensor probe (8) or a plasma discharge wire (50). The oxygen sensor probe (8) is part of an oxygen sensing device (not shown in the figures). With respect to the plasma discharge wire (50), as shown in FIG. 13, the plasma discharge wire (50) is a sharp (less than 200 nm) metal wire that is electrically connected to a device which provides high voltage (HV) pulses. The concentration and type of components in the liquid in channel B can be determined based on the optical emission spectra (OES) produced by the excitation of the plasma discharge (51) at the tip of the sharp metal wire as measured with a spectrum analyzer (53) positioned adjacent to the sharp metal wire. The spectrum analyzer optionally has a fiber optic wire (52).

The pipette probe can further comprise a sensor module in channel A or in fluid connection with channel A. This second sensor provides a baseline concentration of the material in the liquid or baseline temperature of the liquid used to perfuse the single cell for comparison with the concentration of material in the perfused liquid or temperature of the perfused liquid.

Figure 5B:
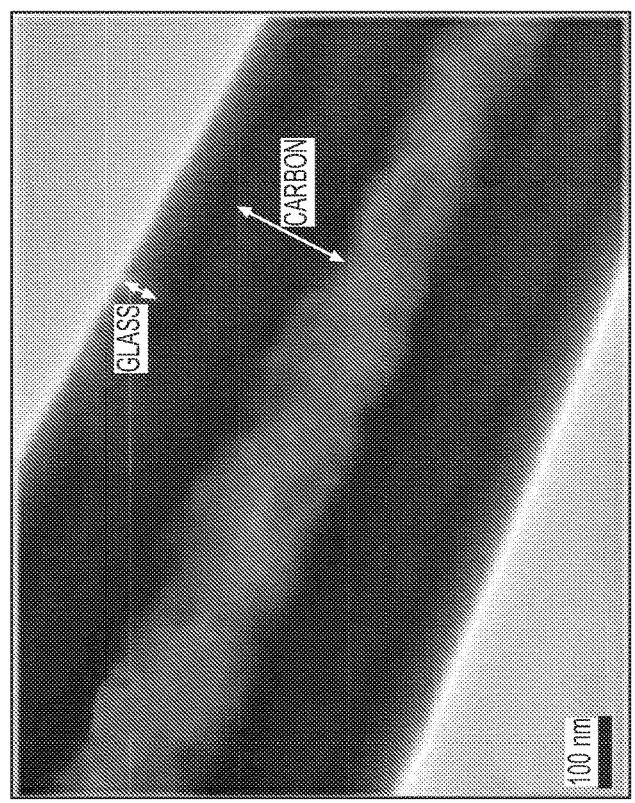
FIG. 5B is a TEM image of a 100 nm scale glass pipette diameter with carbon CVD deposited on the inside walls.
Figure 5A:
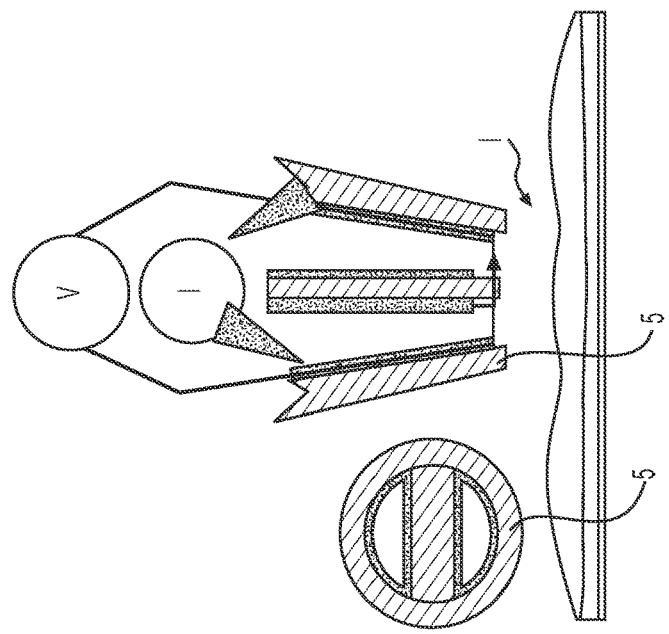
FIG. 5A is an illustration of a theta cross-section pipette with inner walls coated by carbon being used to pass current I through the solution near the pipette tip.

The pipette probe can have a carbon coating (41) on the inner wall (4) of the pipette shaft body (2) as illustrated in FIGS. 5A and 5B. With this design, a small current can be made to travel between the carbon electrodes in the different pipette barrels (channels A and B) to measure resistance that will indicate position of the pipette tip above the cell and/or tissue surface. In addition, this carbon coating (41) can prevent fouling of the walls of channels A and B.

Preferably, the pipette probe has a pipette shaft body (2) which is made of glass.

Figure 17:
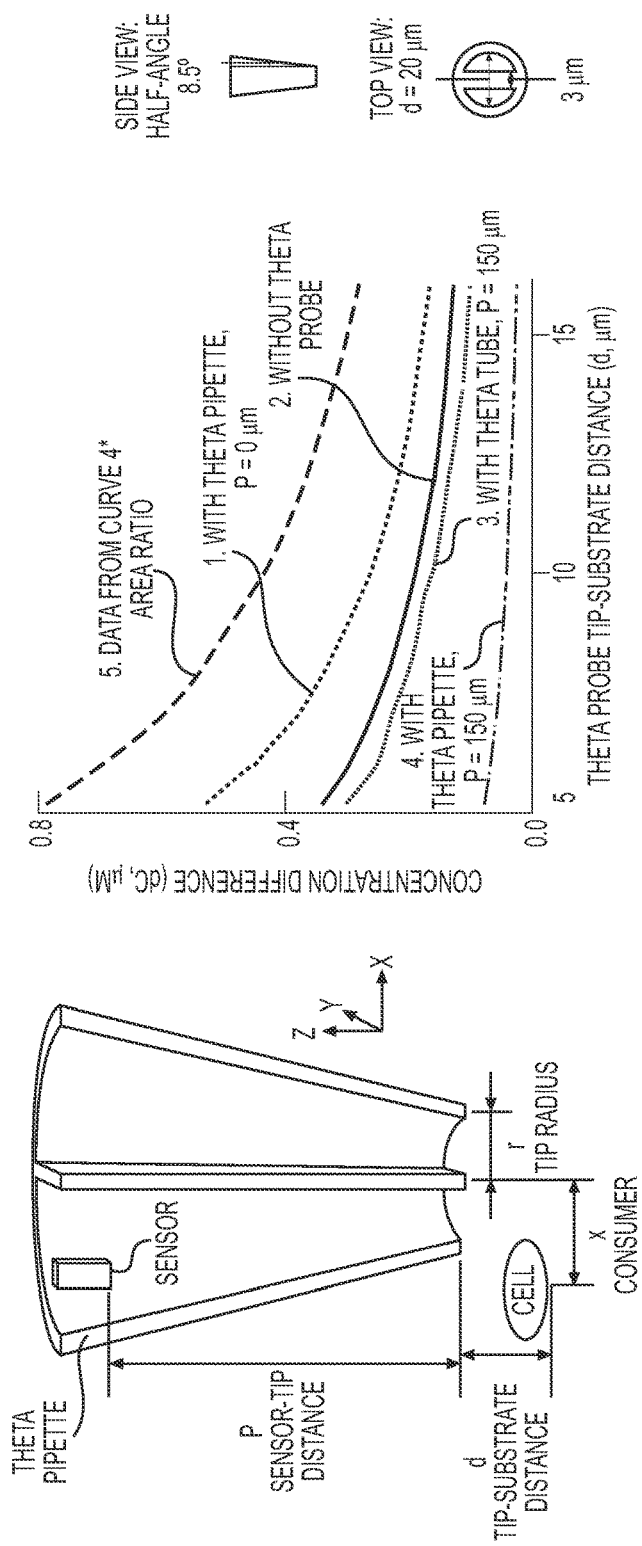
FIG. 17 shows mathematical simulation of geometry parameters, and the dependence of signal (oxygen concentration difference) strength on distance from the theta micropipette tip to the substrate, for different sensor positions, and for different pipette apex angles.

The pipette probe preferably has a conical tip portion. The cone shape allows for a narrow opening at the distal end (5) of the tip, while having increased space for the sensor module positioned above the distal end (5). Many sensors have improved sensitivity based on increased size. This increased space of the conical tip portion is the half-angle. The half-angle is a measure of the angle formed between an imaginary line running parallel to the length of the pipette body (2) and a line formed on the inner wall of the cone of the tip portion wherein the lines intersect at a point halfway between the distal end (5) of the tip and the top of the conical tip portion. Ideally, the conical tip portion has a half-angle of up to 45°, preferably 5 to 30°, more preferably 5 to 20°, as shown in FIG. 17.

Figure 4:
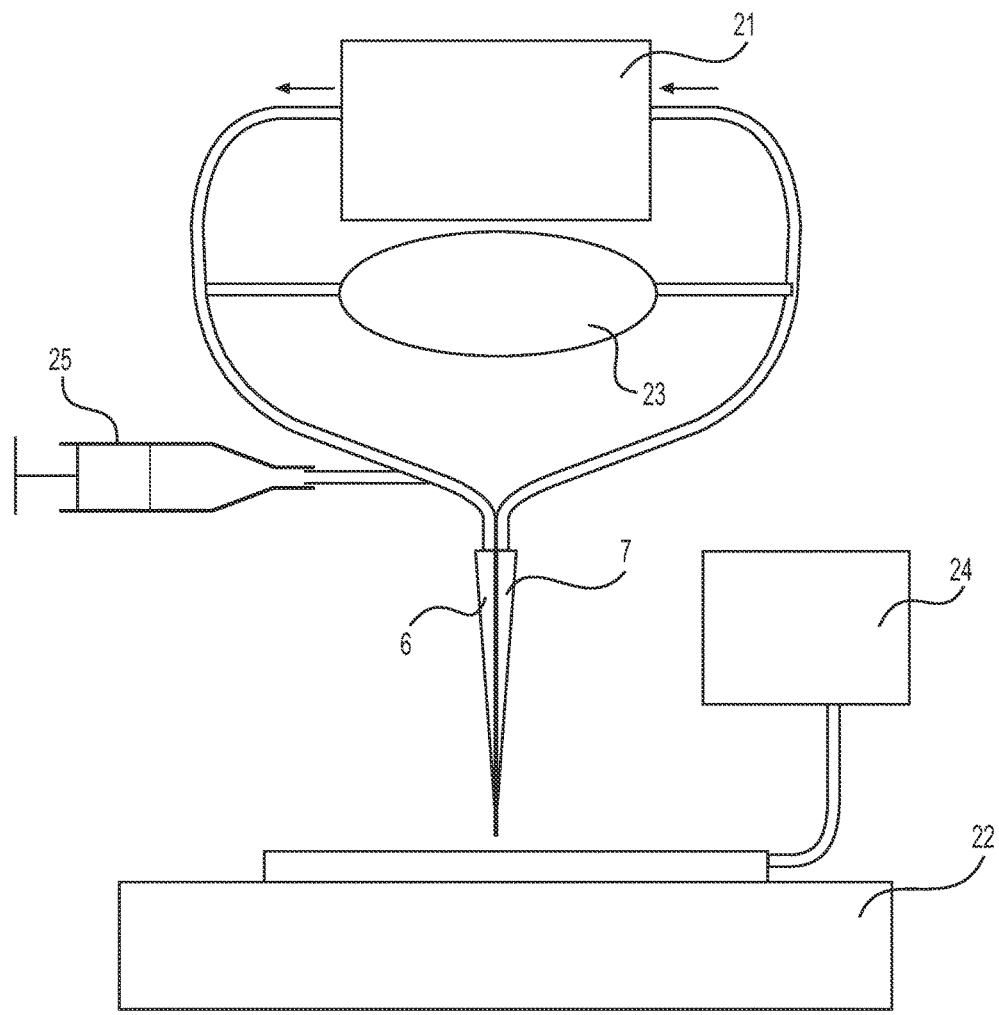
FIG. 4 shows a system diagram for the double barrel pipette probe system.

Double Barrel Pipette Probe System and Method for Perfusing a Single Cell with a Liquid and Measuring the Single Cell's Effect on the Liquid As illustrated in FIG. 4, an aspect of the invention is a double barrel pipette probe system for perfusing a single cell with a liquid and measuring the single cell's effect on the liquid, said system comprising the pipette probe (1), a capillary tube (20) connecting channel A (6) to a fluid pump (21) and a capillary tube (20) connecting channel B (7) to the fluid pump (21), said double barrel pipette probe (1) comprising a pipette shaft body (2) having a distal end (5), wherein the pipette shaft body (2) comprises two channels A (6) and B (7), wherein channel A (6) is configured for flow of liquid out of the distal end of the tip and channel B (7) is configured to receive the flow of liquid exiting channel A (6) at the distal end (5) of the tip, wherein said channel B (7) comprises a sensor module or is in fluid connection with the sensor module for measuring concentration of material in the liquid or temperature of the liquid.

In an embodiment, the pipette shaft body (2) can have a separator wall (3) connecting opposite sides of an inner wall (4) of the pipette shaft body (2), wherein said separator wall (3) is formed in a plane bisecting a lumen of the pipette shaft body (2) in a longitudinal direction, wherein the distal end (5) of the pipette shaft body (2) has a cross section in the shape of the Greek letter theta when viewed from below the pipette shaft body (2), wherein said separator wall (3) separates the pipette shaft body (2) into said two channels A (6) and B (7), wherein channel A (6) is parallel to channel B (7).

In another embodiment, the two channels A (6) and B (7) are coaxial and the pipette shaft body (2) is an outer tube encompassing an inner tube, wherein a space between the outer tube and the inner tube is one of channel A or channel B, and a space in the inner tube is the other of channel A or channel B, wherein the distal end (5) of the pipette shaft body (2) has a cross section which is generally in the shape of the letter O in a circle, wherein there is optionally at least one spacer which maintains the distance between the outer tube and the inner tube.

The capillary tube (20) can be made of any material capable of retaining the fluid in the system. Preferably the capillary tube (20) is made of a pliable plastic such as the plastics used in intravenous tubing.

Another aspect of the invention is a method of using the double barrel pipette probe system for perfusing a single cell with a liquid and measuring the single cell's effect on the liquid comprising positioning said distal end (5) of the tip in proximity to said single cell, maintaining flow of the liquid from channel A (6) having a baseline concentration of material or baseline temperature to channel B (7) at the distal end (5) while perfusing said single cell with the liquid exiting channel A (6), and measuring the concentration of the material in the liquid or temperature of the liquid with the sensor module in channel B (7), comparing the baseline concentration of material or baseline temperature with the concentration of material or the temperature of the liquid as measured by the sensor module, wherein a difference in concentration or temperature values is effected by said single cell. The cell or tissue is maintained in a medium, such as water to maintain the life of the cell. The probe tip is placed in the medium during the measurement.

It is preferred that the pipette shaft body (2) has a conical tip portion narrowing at the distal end (5) and the distal end (5) has a diameter of from about 100 nm to about 100 microns, preferably from about 100 nm to about 50 microns, most preferably, from about 100 nm to about 10 microns. Preferably, the diameter is commensurate with the size of the cell or smaller. The diameter can be from about 250 nm to about 50 microns, or from about 300 nm to about 10 microns.

The double barrel pipette probe system and method of use can include an infusion pump (25) which is in fluid connection with the liquid flowing into channel A and for introducing material into the liquid flowing into channel A. In one aspect, the infusion pump (25) is a syringe pump for introduction of the material into the liquid flowing into channel A. Pulsed perfusion can be controlled on the amount (100-10000 pL) and timing (10-1000 s) of the injections.

The double barrel pipette probe system and method of use can further comprise a motorized computer controlled stage (22) for holding a single cell or a tissue sample and which can move in one or more directions so as to maintain a desired position of the single cell or cells in the tissue sample with respect to the distal end (5) of the pipette shaft body (2).

The double barrel pipette probe system and method of use can further comprise monitoring the pressure of the fluid in channel A (6) and channel B (7) with a component (23) and obtaining desired flow of liquid by increasing or decreasing pressure of the liquid in channel A (6) and channel B (7) with the fluid pump (21).

In an embodiment, the double barrel pipette probe system and method of use further comprises a piezoelectric controlled pipette manipulators and a stage for holding a single cell or a tissue sample, wherein the manipulators grip the pipette and are capable of moving the pipette in one or more directions so as to maintain a desired position of the single cell or cells in the tissue sample with respect to the distal end (5) of the tip.

The double barrel pipette probe system and method of use can include a component (23) for measuring pressure of liquid and is in fluid connection directly or indirectly with channel A (6) and channel B (7) so as to be able to measure the pressure of fluid in channel A (6) and channel B (7).

In an aspect of the invention, the material that is measured comprises at least one of oxygen, alkali metal cation, an alkaline earth metal cation and halide. When oxygen is the material, the liquid may further comprise a respiration modulator. The respiration modulator can be at least one selected from the group consisting of a metabolite, mitochondrial electron transport inhibitor, chemotherapeutic agent, and extracellular pH.

An advantage of the present invention over known systems which encase the single cell is that the flow of liquid perfusing the single cell can be maintained for at least 10 minutes, preferably at least 20 minutes, and if necessary up to many (e.g. 24) hours. The encased systems of the prior art have the disadvantage that the isolated cell starts to dissipate the material so that the concentration of the material contacting the single cell cannot be maintained over an extended period of time.

Figure 7B:
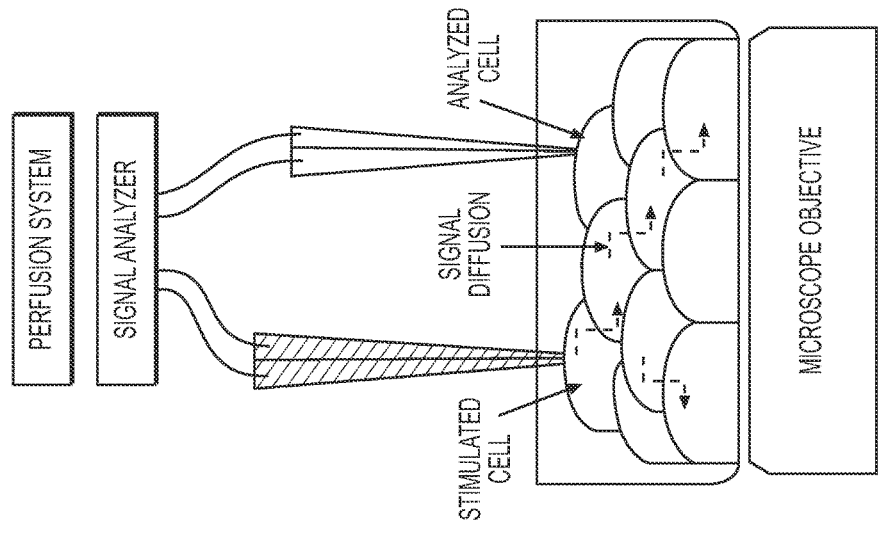
FIG. 7 is schematics of 3-D (A) and 2-D (B) mapping of oxygen consumption protocols on cultured cell monolayer and on tissue slice, respectively.

An advantage of the present invention is that the double barrel pipette probe system can be used to analyze whether perturbation of one cell in a tissue sample will affect other cells in the tissue sample as shown in FIG. 7B. Here, a first double barrel pipette probe is in proximity to a first single cell in the tissue sample, and a second double barrel pipette probe is in proximity to a second single cell in the tissue sample. The second single cell is perfused with a liquid using the second pipette probe, and a baseline of a material in the liquid in channel B of the second pipette probe is determined. Then a modulator (or material) is added to the liquid in channel A of the first pipette probe, and the liquid in channel B of the second pipette probe is measured for any variations.

Figure 7A:
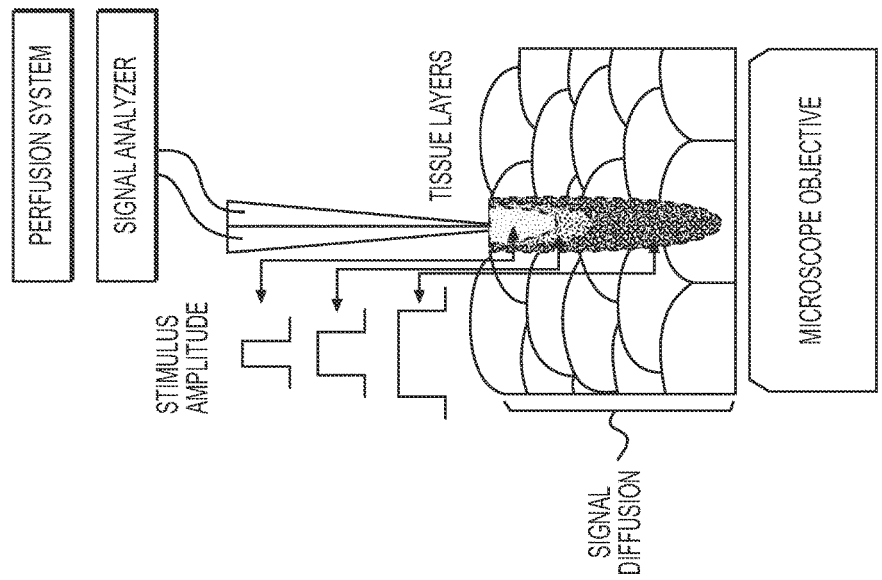

In the alternative, as shown in FIG. 7A, a single cell on the surface of the tissue can be exposed to a modulator at a baseline concentration and/or duration and the depth of response within the tissue cells is measured through the microscope objective, and then the single cell on the surface of the tissue is exposed to a modulator at an increased concentration and/or duration and the depth of response within the tissue cells is measured through the microscope objective. In FIG. 7, the microscope objective is shown below the sample, but in addition or in the alternative, a microscope objective could be placed to the side of the sample.

Any type of cell can be analyzed using the inventive double pipette probe system. However, it is preferred that the cell is an animal cell. Most preferably, the cell is generally oblong or circular in shape. However, other shapes of cells can be accommodated with the use of wells (30) which can isolate the cell.

In practice, the distance from distal end (5) of the tip to the substrate (43) can be optimized to give the maximum signal, and is preferably less than 20 microns, more preferably less than 10 microns, and most preferably ≤5 microns. It is preferred that the distance from the distal end (5) of the tip to the substrate is significantly smaller than the diameter of a lumen of the tip.

The single cell can be positioned within 20 microns of an imaginary line which is at the center of the pipette shaft body (2) and runs parallel to the length of the pipette shaft body (2), preferably, within 5 microns, most preferably said imaginary line also runs through the single cell.

In the inventive double barreled pipette probe system, the sensor module is positioned wherein the sensor module is positioned up to 2 mm from the distal end (5) of the tip, optionally 100 microns to 2 mm from the distal end (5) of the tip, and optionally 150 microns to 2 mm from the distal end (5) of the tip. The distance that the sensor module is positioned from the distal end (5) of the tip depends on the type and size of the sensor module.

In an aspect of the invention, the distal end (5) has a diameter which is no more than 5 microns greater than the diameter of the single cell or the maximum diameter of a single cell in a tissue sample (9), preferably no more than 1 micron greater than the diameter of the single cell or the maximum diameter of a single cell in a tissue sample (9), more preferably the distal end (5) has a diameter which is ±100 nm of the diameter of the single cell or the maximum diameter of a single cell in a tissue sample (9). In an embodiment, the diameter of the distal end (5) of the tip is smaller than the single cell.

Figure 16:
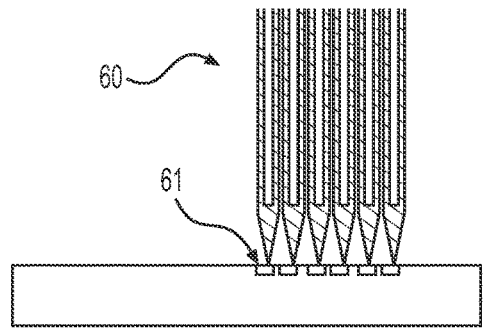
FIG. 16 shows extensions of the double-barrel pipette probe as a perfusion respirometer to cell array respirometry.

In an aspect of the invention, an array of double barrel pipette probes (60) is used as shown in FIG. 16. Here, single cells are isolated in an array of wells (61) or are surface cells of a tissue sample, and more than two double barrel pipette probes (60) are each used to perfuse different single cells, and the difference in concentration or temperature values effected by each single cell is collected.

Fluid in one of the pipette barrels (6) (also herein referred to as "channel A") is forced to flow toward the cell on the substrate (43) or tissue surface, while the fluid is also forced to flow away from the cell on the substrate (43) or tissue surface at the same rate in the other pipette barrel (7) (also referred to herein as "channel B"). In this way, when the open tip at the distal end (5) of the double-barrel pipette probe (1) is placed above a cell on the substrate (43) or tissue surface, the fluid moves past the cell bringing new oxygen and other molecules through the incoming fluid from channel A (6) and taking the remaining oxygen, remaining molecules of the incoming, fluid as well as any products of respiration that the cell might emit through the outgoing fluid in channel B (7). The sensor module shown in FIG. 1 is an oxygen sensor (8). However, different types of sensor modules can be used to measure the amounts of other molecules or ions present in the incoming and outgoing flows of fluid. By sensing oxygen and possibly other molecules or ions in the incoming and outgoing flows of the fluid, oxygen consumption by the cell can be quantified either alone or together with consumption or production of other molecules.

Figure 12:
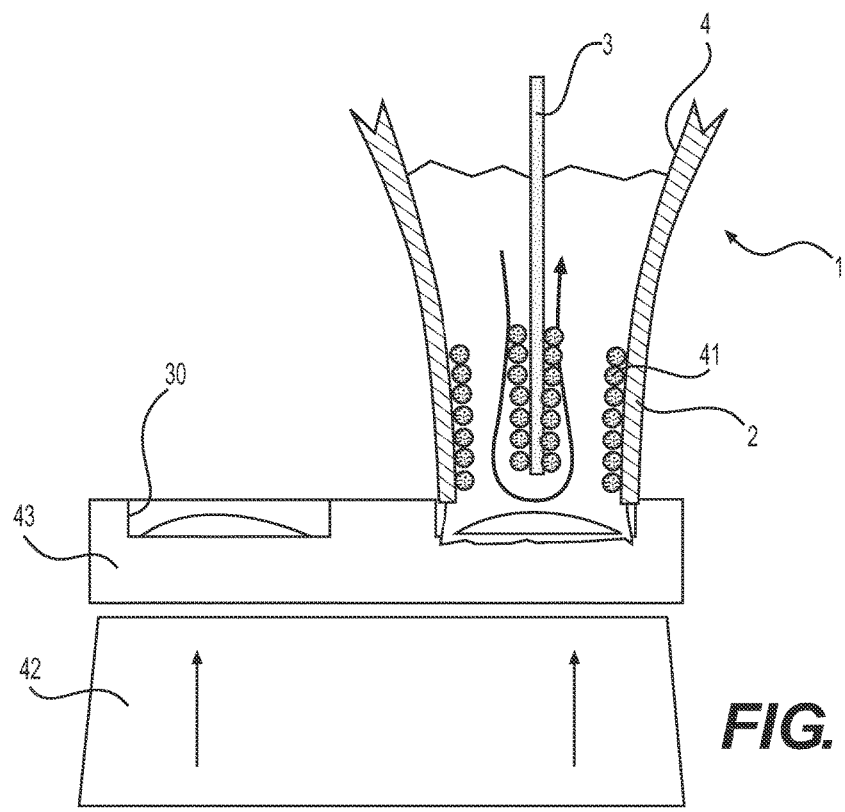
FIG. 12 shows a diagram of oxygen detection with the double barrel pipette probe.

In one embodiment of oxygen sensing within the double barrel pipette probe, the sensor module is a fluorescent material (41) deposited on the inner walls (4) of the pipette shaft body, see FIG. 12. Fluorescence lifetime or intensity can subsequently be employed as a measure of oxygen content. Oxygen changes fluorescence lifetime and intensity by providing a means for quenching fluorescence. Fluorescence of the material deposited on the inner surfaces of the pipette can be excited and measured through a microscope objective (42), which is particularly convenient when the cellular substrate is highly transparent and the microscope objective is positioned below the substrate (43). In FIG. 12, single cells (30) are shown to be isolated on the substrate (43). However, it is also possible to perfuse single cells in a tissue sample on the substrate (43). In an alternative embodiment, the sensor module is a commercially available fibemptic oxygen sensors which can be placed within one or both of channels A and B.

Injection of various molecules plays an extremely important role in currently available respirometers designed for many thousands to millions of cells. Using the same widely established methodology for single cell measurement is highly desirable and is possible with the inventive double barrel pipette probe system. The double-barrel pipette probe system utilizing perfusion for single cell respiration measurement disclosed here provides the possibility to add different molecules that can modulate cell respiration into the incoming flow in channel A (6). At the same time, the double-barrel pipette probe system utilizing perfusion permits to maintain constant cellular environment in order to Observe cell respiration over the periods of at least 10 minutes, preferably, at least 20 minutes, and if necessary up to many (e.g. 24) hours. Furthermore, the double-barrel pipette probe of the present invention can be used not only with cells separated and placed onto substrates (43), but also on cells that are naturally present on surfaces of tissues.

The ability to measure respiration of individual cells in tissues permits inference of the effect of cell-to-cell interaction on cell respiration. It may also provide mechanisms to study the effect of cell-to-cell signaling on respiration, see FIG. 7.

An embodiment of this invention is that the double barrel pipette probe system can be used as a respirometric microscope for mapping metabolic activity on living tissues with a single cell spatial resolution and a few seconds time resolution. Monitoring changes in cellular respiration due to variations of metabolites, mitochondrial electron transport inhibitors, chemotherapeutic agents, extracellular pH or other factors provides insight leading to important conclusions regarding mitochondrial state and dysfunction associated with a number of diseases. The inventive instrument is based on scanning of a probe creating localized flow (perfusion) that will measure oxygen flux at different tissue locations directly and permit the investigation of both lateral and through tissue diffusion and signaling which regulate metabolic activity (see for instance FIG. 7).

Tissue and cell culture respirometers have been developed and are commercially available today from multiple companies. They are widely employed in biological studies and in diagnosing diseases such as neuromuscular dystrophy. Thus, needs and methodologies for respirometry are well established. However, the existing tools are suitable for determining average respiration only from relatively large collections containing at least $10^5$-$10^6$ cells and no tool exists to map respiration of living tissues at a single cell level, as in the present invention.

Design, Fabrication, Control and Calibration of the Scanning Perfusion Probe

With respect to spatial resolution, one important role of the double-barrel pipette probe is to increase sensitivity by placing a sensor further up the pipette and using the perfusion flow, while preserving spatial resolution to permit measurements from individual cells in a cell culture. FIG. 3 illustrates that high resolution is achievable. In fact, it shows that the resolution is on the order of the pipette diameter and, since diameters smaller than micrometers are readily achievable, the resolution on the order of micrometers is possible.

Figure 3A:
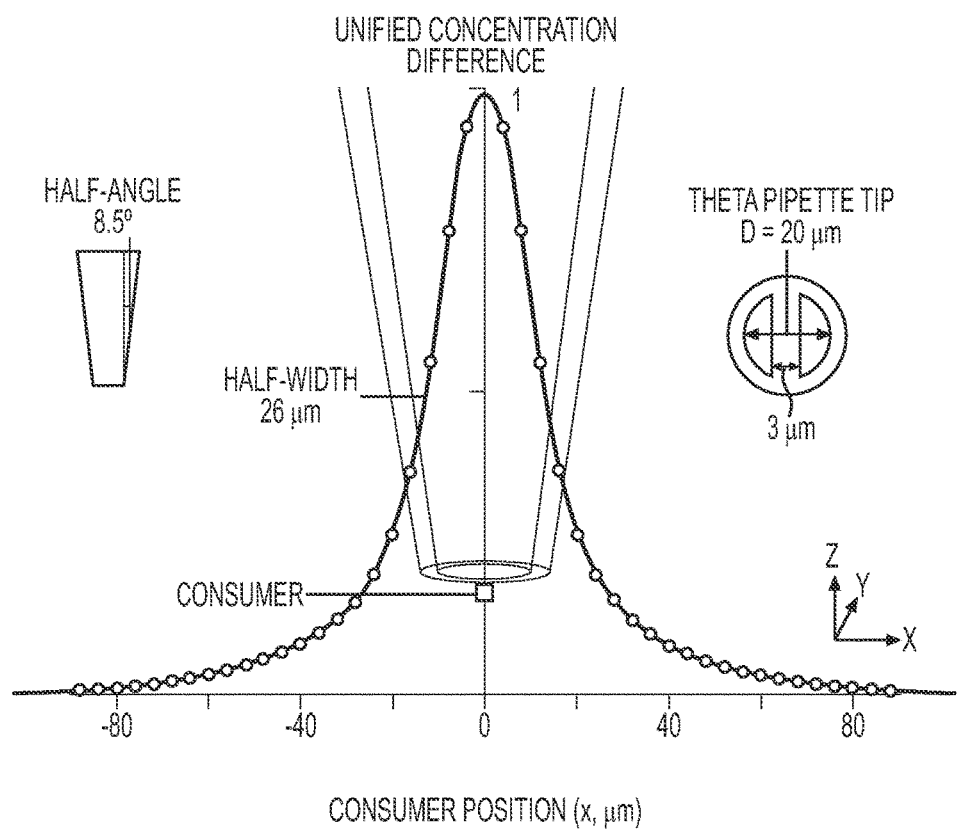
FIG. 3 shows results of spatial resolution of a scanning double barrel pipette probe using mathematical modeling.

In FIG. 3A is an illustration of spatial resolution of the inventive double barrel pipette probe as a perfusion respirometry probe with a tip diameter of 20 µm. The data in the graphs were obtained assuming that the probe is located at the center of the x axis and the having the specific tip geometry (as in insets). The oxygen concentration difference is the aimed signal, and is measured by a sensor module inside the probe, 150 µm above the tip. A consumer (or single cell) size of 2×2×2 µm³ is located at the substrate. The distance from substrate to theta pipette tip is set to 6 µm. The pressure applied at input channel is (1 atm+2 Pa), and at the output is (1 atm−2 Pa). With these pressure setups the perfusion improves the signal most significantly. In FIG. 3A, the curve is a plot of the measured signals as the center position of the consumer moves from left (x=−90 µm) to right (x=90 µm) along the x-axis. The half-width of this curve is 26 µm, and can be defined as the spatial resolution.

Figure 3B:
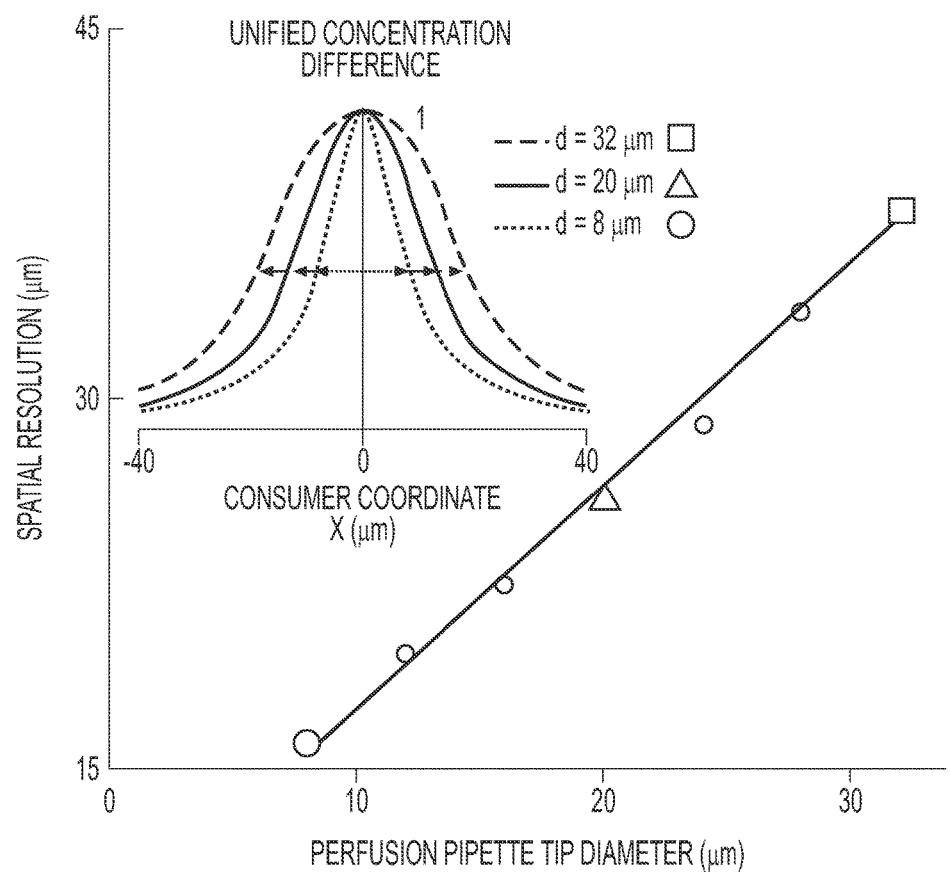

In FIG. 3B, is a graph of the probe spatial resolution vs. tip diameter. Here, the pressure at the inlet and outlet of the theta pipette is set to achieve the best improvement of signal at 150 µm above the tip for each tip diameter, respectively. The theta pipette tip diameter increases from 8 µm to 32 µm with a step size of 4 µm while the half-angle of the pipette is kept the same (8.5°). The graph in the inset of FIG. 3B shows the oxygen concentration difference plot at tip size=8, 20 and 32 µm.

Double Barrel Pipette Probe Fabrication

Glass capillaries of theta shaped cross section (as illustrated in the inset of FIG. 5A) are typically 1.5 mm outer diameter and can be purchased from Sutter Instrument Co. A pipette puller, such as the P-2000 pipette puller from Sutter Instruments, can be used to reduce the tip size, while retaining the same theta cross section. The double barrel pipette probe can be made of any sturdy material, but it is preferred to use glasses such as silica, aluminosilicate, borosilicate or quartz. The size of the columnar glass capillaries for use in preparing the double barrel pipette probe is not particularly limited, but the pipette body can have: a)

an inside diameter of 0.25 mm-1.6 mm, optionally 0.5 mm-1.2 mm, or 0.5 mm-1.0 mm; b) an outside diameter of 0.8 mm-2.0 mm, optionally 1.0 mm-1.75 mm, or 1.2 mm to 1.6 mm; c) a wall thickness of 0.2 mm-1.0 mm, optionally 0.3 mm-0.8 mm, or 0.5 mm-0.75 mm; and d) an overall length of 3 cm-15 cm, optionally 5 cm-15 cm, or 7 cm-12 cm. During the pipette pulling, the ends of the glass capillaries are pulled apart, while the middle of the capillary is heated by a laser. Depending on the pulling rates and the total pulling length, the sizes of the two pipette barrels at the outlet can be varied from 100 nm to 100 microns. FIG. 5A shows a nanoscale single barrel pipette with a carbon coating. This same type of coating can be used on the inner walls of the inventive double barrel pipette probe. The conical angle of the pipette is also controlled by the pulling parameters. Pipettes whose diameters increase relatively quickly from their tips are more robust in operation. Conical angles (i.e., the half angle) of up to 45 degrees can be used, preferably 5 to 20 degrees, more preferably 5 to 15 degrees can be used. Such pipettes can have each of their barrels increased to about 200-250 µm within about 1-2 mm away from the end. This will permit positioning of sensors, such as fiber-optic oxygen sensor, at a distance of about 1-2 mm away from the tip. Each pipette barrel will be connected to pumps, pressure sources or sensor, which control the injection and extraction pressures and flow rates. Teflon tubing can be employed for the capillary tubes and sealed using epoxy (or other type of adhesive).

Oxygen Confinement Due to Pipette and Effect of Pipette Diameter Expansion

One influence of the pipette is confinement of oxygen diffusion within it. Oxygen can diffuse freely along the pipette axis (z axis as in FIG. 17A), but remains confined by the pipette walls. To demonstrate the effect of this confined diffusion, consider a small oxygen sensor module (or simply "sensor") positioned at a small distance from the cell. The geometry parameters used in the model are demonstrated in FIG. 17A. The FEM simulation results are shown in FIG. 17B. Curve 1 is plotted from a sensor located at the tip of a typical theta pipette which has a half-apex-angle of 8.5 degrees, and a tip diameter of 20 µm; Curve 2 is from a sensor at the same location, but without a theta pipette surrounding it; Curve 3 is from a sensor located inside a theta tube and 150 µm above the tip. This theta tube has a apex angle of 0°, and a tip diameter of 20 µm; Curve 4 is a plot from sensor located inside typical theta pipette and 150 µm above from its tip; Curve 5 (unit less) is a plot of same date of curve 4 multiplied by the area ratio of this location compare to tip position. In FIG. 17B (curve 1 vs. curve 2), oxygen concentration difference signal (oxygen concentration measured at the sensor refers to the oxygen concentration at top of the double-barrel pipette) obtained by the sensor positioned at the tip of the pipette has around 1.5 times greater signal than the same size sensor placed at the same distance away from the cell, but without any pipette. Thus, the mere presence of the pipette over the cell increases the oxygen concentration difference that can be sensed. FIG. 17B also shows that moving the same sensor within the pipette much further from the cell, while maintaining the same distance of the pipette tip from the cell, reduces the signal as might be expected. Most of this reduction can be attributed to the expansion of the pipette diameter away from the cell due to a non-zero pipette apex angle. This conclusion can be confirmed by considering a theta pipette with a zero apex angle (theta tube, curve 3 in FIG. 17B). As demonstrated in FIG. 17B, the signal obtained by a sensor placed 150 µm away from the tip of the theta tube is nearly the same as the signal obtained by placing the sensor close to cell without the tube (curve 2 in FIG. 17B).

An advantage of the use of the conical tip of the inventive double chamber pipette probe, is that the diameter of the pipette expands away from the tip (in case of a non-zero apex angle), and as such the sensor modules used in the channels can increase in size. If the sensor area is scaled with the expanding pipette diameter, the signal can be improved significantly depending on the nature of the sensor. For example, electric current as the signal in electrochemical sensors is proportional to the effective sensor area. If the sensor sensitivity is taken to be proportional to the area, one can significantly increase the overall sensitivity of the probe as one moves the sensor further away from the pipette tip, which is also indicated in FIG. 17B (curve 5 vs. curve 1). Therefore, this analysis suggests an opportunity to improve sensitivity without sacrificing resolution.

One may wonder why the signal strength is increased when the concentration decreases in a pipette that increases its diameter along its axis (z axis as in FIG. 17A). Diffusion along non-zero apex angle pipette which increases its diameter along its axis proportionally to the axial distance can be modeled as a diffusion in a solid angle of a sphere. Such model would yield concentration that decreases linearly with the axial distance. At the same time, the sensor area would increase as square of the axial distance resulting in a linear gain of sensitivity with distance for a sensor whose sensitivity is proportional to its area.

Pipette Surface Functionalization for z-position Control and Antifouling

As shown in FIG. 5B, carbon can be deposited on the pipette walls by Chemical Vapor Deposition (CVD). Such pipettes can be used in the electrochemical sensing in extremely small fluid volumes. As illustrated in FIG. 5A, a small current can be used between the carbon electrodes in the different pipette barrels to measure resistance that will indicate position of the pipette tip above cell and/or tissue surface. The advantage of using carbon coating, rather than placing wires into the pipette barrels, is in the possibility of bringing the electrodes closer to the tip. The voltage signal from the carbon electrodes will be sensed and the closeness to the substrate in the z-direction can be determined and controlled. As an alternative or in addition to, the use of pressure sensing (as illustrated in FIG. 4) can be used to control the z-position. Pressure sensing will also be convenient to detect any fouling that might occur within the pipette barrels. Nonspecific adsorption of proteins is a crucial problem in the development of microfluidic tools. As an approach to antifouling coatings, the pipette surface can be modified with zwitterionic antifouling films by CVD. For instance, pol-2-(dimethylamino) ethyl methacrylate-co-ethylene glycol dimethacrylate] (PDE) thin films can be synthesized by CVD and these films can be reacted with 1,3-propane sulfone to obtain the zwitterionic structure. The cross-linker ethylene glycol dimethacrylate (EGDMA) can be used to make the copolymer insoluble in water. Zwitterionic coatings will reduce nonspecific adsorption.

Overall Design of the Fluid Handling in the System

In the fluid handling aspect of the inventive double barrel pipette probe system, the fluid flow is controlled. This can be done by pressure or by pumps controlling fluid flow. The pressure difference in the fluid travelling to the consumer and the fluid traveling away from the consumer provides feedback information indicating hydraulic resistance that will be related in part to the proximity of the pipette tip to the surface. Also, in the fluid handling aspect of the inventive double barrel pipette probe system that contains ports for injection of metabolic modulators (as shown in FIG. 4). Standard tubing can be used with ports that could be coupled to syringe pump(s) or infusion pump(s). Pulsed perfusion uses fine control on the amount (100-10000 pL) and timing (10-1000 s) of the injections.

Oxygen Sensing

When the double barrel pipette probe is used to measure oxygen consumption of the single cell, two oxygen concentration sensors (sensor modules) can be used in every probe to provide oxygen flux signal ($S=c_o-c_\mu$, eq. 3). These sensors may be placed within the pipette barrels (channels A and B) at a distance of about 1-2 mm away from the tip. These sensors can be optical and/or electrochemical in function. The optical sensors typically rely on changes of luminescence quenching time in the presence of oxygen. Such optical sensors exist in molecular, nanoparticle and fiber-optic forms. On the other hand, in the molecular and particular form, intra- and/or extra-cellular oxygen sensing can be used, although the drawback is the lack of distribution uniformity of the molecules within cells and tissues. Similar sensing can be employed in measurement of respiration activity of separated cells sealed into substrate microwells in a cell array format. Commercial fiber-optic sensors (for example OXB50 from Pyroscience, 50 µm diameter) are available together with the excitation/readout system designed for multiple fiber-optic probes. To measure quenching time, luminescence is excited using a periodically modulated light (typically blue), while a phase delayed sinusoidal signal is obtained from the fluorescent reporters (typically red). The phase delay between the excitation and fluorescence emission is indicative of the amount of oxygen near the fluorescent reporter. When multiple fibers employ the same excitation signal, their emission phases can be compared to provide a differential measurement of the concentrations. As an alternative, the flow velocity can be modified.

Electrochemical devices for oxygen sensing can be employed as scanning probes to measure oxygen concentration. The primary challenges with these include sensitivity to probe distance from the cell surfaces and non-negligible consumption of oxygen by the probe itself.

The double barrel pipette probe system can be calibrated to measure oxygen consumption response function. Electrochemical probes can be used, which consume oxygen or pipettes which inject oxygen into a lower oxygen concentration solution as sinks and sources of oxygen consumption in this calibration procedure. Under the microscope, the perfusion probe can be scanned over the sink or source to map out the oxygen consumption response.

Hydrodynamic Confinement

Consider flow within a long channel. A molecule could not diffuse outside the channel due to the presence of hard channel walls. However, if the channel walls are missing along some length segment of the flow, the molecule might diffuse outside, unless the flow sweeps it through this section before it has a chance to exit. Therefore, in the section where channel walls are missing, like the section at the tip of the double-barrel pipette, the molecule could remain confined to the flow hydro-dynamically. The time that it takes a molecule to diffuse across the section of length b along the flow is $b^2/D$, where D is the diffusion coefficient, while the time it takes the flow to cross the same distance is roughly b/v, where v is the flow velocity. Taking the ratio of these times, one can obtain the Peclet number $P=bv/D$ which indicates the relative importance of convective transport (flow) over the diffusion. When the Peclet number is large, the diffusion time is larger than convective transport time and the likelihood that a molecule would remain confined in the flow is large.

Experiments of hydrodynamic confinement at the tip of the theta cross-section double-barrel pipette compare well with a FEM (Finite Element Method) Model that implements both Navier-Stokes equations to model the fluid flow and convection-diffusion equations to model molecular diffusion. In the experiment, the fluid is being withdrawn at a fixed rate through one channel, while different pressures are applied to the injection channel. Two qualitative trends can be noted. One is the increasing size of the fluorescent plume with the increase in the pressure applied to the injection channel.

Figure 11:
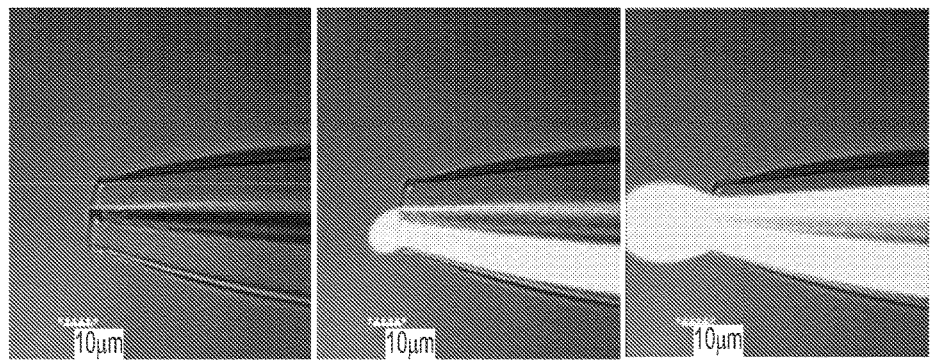
FIG. 11 shows a double-barrel pipette probe with theta-like cross section, wherein Rhodamine 6 G solution is employed to observe the flow using fluorescent microscopy.

In general, it is clear that the size of the plume can be varied from being smaller than the size of the pipette tip to being somewhat larger, see for instance, FIG. 11. The other trend is the change in the tilt of the diffusion plume with the increasing pressure applied to the injection channel. Somewhat counter intuitively, at lower injection pressures the plume tilts away from the extraction channel, while at higher pressures it begins to tilt toward the extraction channel. The average dye concentration in the extraction channel also increases as the plume tilts toward that channel. It can be seen that the injection pressures at which size and shape of the plume in the FEM model matches the experimental observations, suggesting that the model is fairly accurate.

Flow calibration at the tip of the double-barrel pipette can be carried out using fluorescent dye, such as Rhodamine. By setting different out- and inflow rates, it is possible to observe at which rates and, therefore, at which average flow velocities most of the dye will flow through and when diffusion of the dye would be minimized. An example of this technique is illustrated in FIG. 11. FIG. 11 shows double-barrel pipette probe with theta-like cross section having approximately 8 µm size at the opening of each barrel corresponding to about 100 square microns of cross section area per barrel and unequal flow rate in each barrel controlled separately. Rhodamine 6 G solution is employed to observe the flow using fluorescent microscopy (fluorescent pictures superimposed on bright field for the purpose of visualization). Flow begins to dominate diffusion when velocity in each barrel reaches about 25 µm/s. This is in good correspondence of $4\times10^{-6}$ cm$^2$/s as the dye's diffusion coefficient. In the left picture of FIG. 11, zero outflow and inflow rate is applied. Slight fluorescence in the bottom barrel can be observed due to the diffusion of the dye. In the middle picture of FIG. 11, outflow in the bottom barrel of 250 pL/min with the inflow of 100 pL/min. Size of the plume increased as expected. Some diffusion of the dye occurs, but a significant amount is withdrawn into the upper barrel. In the right picture of FIG. 11, outflow of 500 pL/min with the inflow of 400 pL/min. The size of the plume is enlarged as expected and its shape evens out due to significant proportion being taken up in the upper barrel.

Using the information provided herein, the outflow and inflow rates can be optimized based on the particular cell type and analyte being observed and the diameter of the probe tip. Preferably, the outflow and inflow rates are individually set at 50 pL/min-750 pL/min, more preferably, 50 pL/min-600 pL/min, and most preferably 50 pL/min-550 pL/min. Optionally, the outflow and inflow rates are individually set at 100 pL/min-600 pL/min, or 200 pL/min-550 pL/min.

Effects of Perfusion on Oxygen Consumption Signaling

Figure 18:
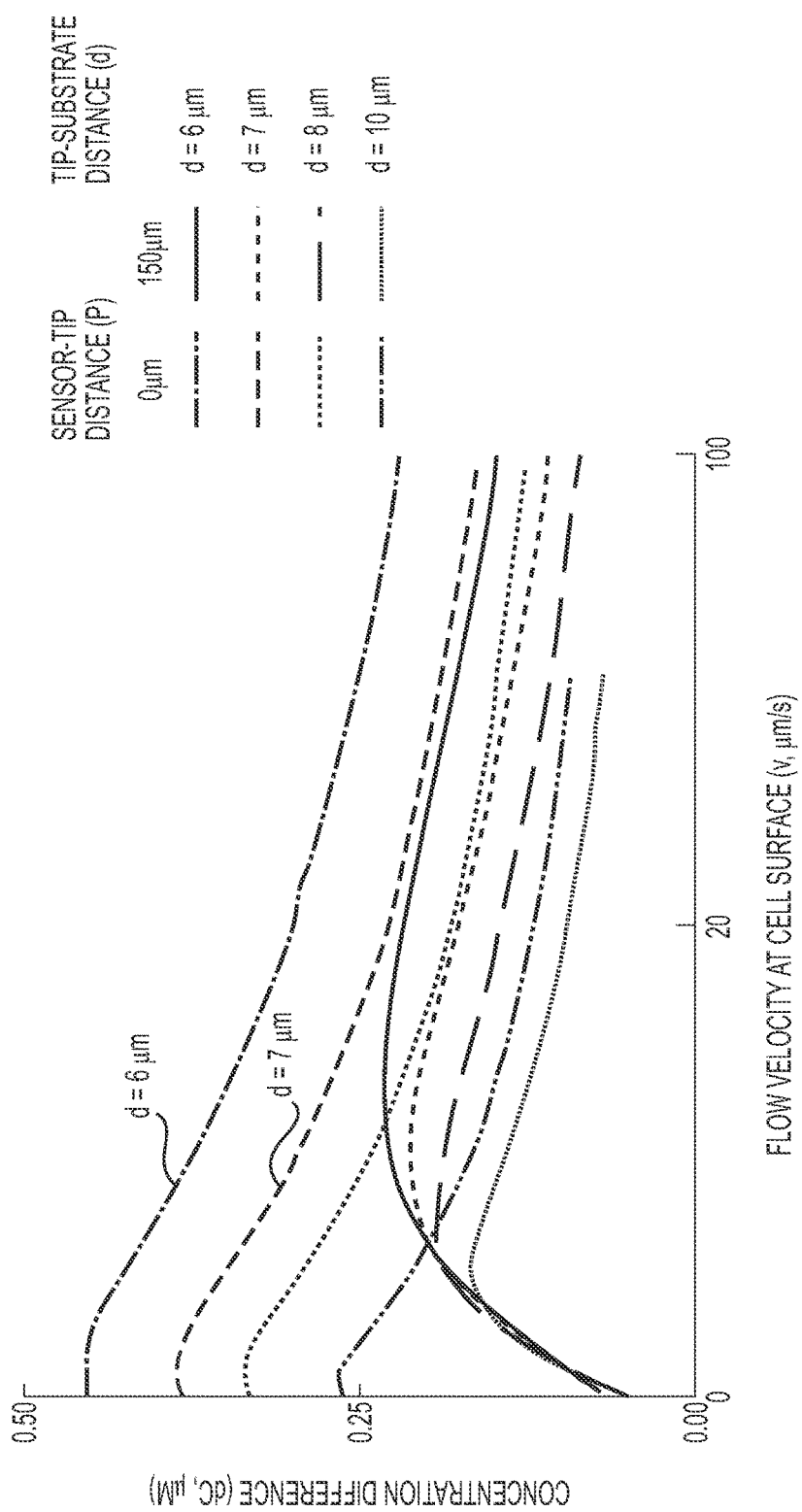
FIG. 18 is a graph showing dependence of signal (oxygen concentration difference) strength on perfusion flow velocity for different tip-substrate distance, and for sensors at different locations (0 μm and 150 μm above the tip) inside the typical theta pipette (tip diameter=20 μm, half-angle=8.5 degree).

Perfusion has been demonstrated, both theoretically and experimentally to hydrodynamically confine molecules within the flow. Intuitively, one may expect that losing less molecules to the diffusion away from the sensor should increase the probe sensitivity. As shown in FIG. 18, this effect is indeed confirmed by the FEM calculations when considering a sensor placed 150 μm downstream within the double-barrel pipette. One would expect significant amplification of the signal (oxygen concentration difference) due to perfusion to occur when diffusion dominates over the convection and the Peclet number is significantly smaller than 1, say 0.1, since in such a regime of operation all oxygen molecules are not fully retained within the flow and increases in flow velocity help retain oxygen molecules. At larger flow velocities most oxygen molecules are already confined to the flow and further velocity increases do not amplify the signal. This logic can provide a rough estimate of perfusion velocity range beyond which no signal is gained. As an example, one can consider the pipette that is located at about b=10 μm from the substrate. Taking the oxygen diffusion coefficient of about 2000 μm$^2$/s and assuming that amplification occurs mostly below the Peclet number of 0.1, one finds that no significant signal gain should occur beyond the velocity $v_{max} \approx PD/b = (0.1 \times 2000)/10 = 20$ μm/s. This is in quantitative agreement with the velocity of maximal signal calculated by the FEM and shown in FIG. 18.

FIG. 18 shows the dependence of signal (oxygen concentration difference) strength on perfusion flow velocity for different tip-substrate distance, and for sensors at different locations (0 μm and 150 μm above the tip) inside the typical theta pipette (tip diameter=20 μm, half-angle=8.5 degree). The group of dotted curves are measured from the sensors at the tip of theta pipette; the group of solid curves are from sensors inside the theta pipette, and 150 μm above the tip. For both groups, the distance from the theta pipette tip to substrate increases.

Intuition also suggests that, as the velocity increases further, the flux of oxygen in the pipette due to flow should start to dominate the flux due to oxygen consumption, reducing the oxygen concentration difference along the z-axis of the extraction channel. The reduction of oxygen concentration difference between different positions along the flow at higher flow velocities can be demonstrated by a simplified analytical model and given by Equation (1):

$$S = C_0 - C_d(x) \approx \frac{Rb}{v}\left(\exp\left(\frac{v}{D}d\right) - \exp\left(\frac{v}{D}x\right)\right) \propto \frac{Rb}{v} \quad (1)$$

where R is the oxygen consumption rate per unit length of the flow, b is the length of the oxygen consumption region in the flow, c>>b is the distance from the tip of the pipette to the place in the flow where a constant oxygen concentration $C_0$ exists due to contact with the environment, x is the position of the sensor downstream from the consumption region and $C_d(X)$ is the oxygen concentration measured by the sensor.

The effects of probe operation and chamber perfusion on cells and tissues can be measured. The system operation has the potential to perturb cellular behavior and an object of the invention is to minimize these perturbations. Initial testing can be carried out on cultured human prostate cancer cells for which mitochondrial metabolism is predetermined by other methods. The effects can be determined of chamber perfusion, of probe perfusion and of current-based probe position control on cytosolic calcium perturbations (using fluo-4 AM fluorescent probe) as the perfusion response. The perfusion parameters that are least disturbing to the cellular homeostasis can be determined. Minimally disturbed cells are expected to produce negligibly small and fast recovering cytosolic calcium elevation. Mouse brain tissue slices having a thickness of from 100-150 μm can be used in the test. The tissue preparation effects together with the effects of chamber and probe perfusion can be examined using calcium probes similar to those used in cell cultures. Additionally, to prove functional integrity of the prepared and perfused slices, the cells can be exposed to external stimuli, such as ATP, to monitor the level and recovery of the baseline activity of cellular calcium signaling.

The effects can be examined of cell and tissue environments on the operation of the inventive double-barrel pipette probe in scanning perfusion probe respirometric microscopy. Cell and tissue environment may pose challenges to operation of the probe and appropriate operational strategies can be used to overcome these issues. Problems with fouling, suction of debris into the probe and effects of chamber perfusion can be avoided/reduced by the ability to reverse the probe flow direction. In addition, any issues can be overcome relating to effects of tissue and cell chamber perfusion flow on local perfusion probe measurements. The tissue chamber average flow velocity can be 25 mm/s. For a fluid layer of thickness d~5 mm typical for the chamber, approximate velocity distribution as a function of distance z from the tissue surface is $V=V_{ave}z/d$. Thus, at a distance of about z=5 μm, the chamber perfusion flow velocity is expected to be around 25 μm/s which is comparable to the local perfusion flow speed created by the probe. Therefore, the chamber perfusion flow may diminish the overall resolution and sensitivity. As part of the present invention, Comsol Multi-physics Finite Element package is used to model these effects and compare these models to the oxygen concentration measurements on cells and tissues. First, cell culture measurements are made because such measurements can be performed with and without chamber perfusion. Subsequently, similar measurements can be carried out on mouse brain tissue slices. As an alternative to continuous chamber perfusion for tissue support, an intermittent chamber perfusion can be carried out between measurements. Standard respirometry protocols for intact and permeabilized cells can be obtained.

2-D and 3-D Diffusion and Signal Transmission Mapping

One of the key limitations of conventional respirometry is its ability to measure metabolic activity of cells below the tissue surface and to determine second-order effects related to how cells may modulate each other's functional activity. The inventive respiration microscopy as shown in FIG. 7 allows one to measure non-invasively and over microscopic dimensions 3-D oxygen consumption profiles as well as to evaluate the extent to which neighboring cells influence each other. Localized perfusion enables mapping of metabolic activity due to signaling and diffusion through tissue. Tissues may differ from each other and from one location to another not only in the cellular phenotypes, but also in their structure resulting in possibly different transport mechanisms of various molecules that would affect metabolic activity. The ability to pulse perfuse a metabolite or a metabolic modulator in one location using one perfusion probe and permitting different depth and radius of penetration, while mapping time varying respiration with another perfusion probe will permit to map diffusion and metabolic cell signaling with cellular resolution. Concurrent confocal microscopy will permit simultaneous measurements of depth and radius of penetration of the metabolic stimulant or modulator. This type of functional microscopy is new and provides information on 3D structure and function of tissues as well as dynamics of its response.

To study 3-D oxygen consumption profiling capability, the tissue is perfused with naturally fluorescent Curcumin, which is known to affect mitochondria. Different Curcumin concentrations and times of exposure to the tissue surfaces will result in its different tissue penetration, which will be monitored through confocal microscopy while performing scanning perfusion probe respirometry (FIG. 7A). Different Curcumin penetration on the same tissue slice is expected to result in different respirometric response at the same probe location yielding information regarding respirometry of different tissue layers. Using this method, one can obtain the probe response as a function of tissue depth as well as lateral probe position. Having found this response function, oxygen consumption in 3-D can be studied by employing deconvolution.

Another aspect of the invention, employs two local perfusion probes at different locations over cell monolayer or tissue slice in order to study how local modulation of metabolic activity of one cell affects metabolic activity of distant cells (FIG. 7B). In this case, one probe will be used to introduce a stimulant, such as ATP or Thapsigargin, locally and the second probe will be employed to measure respiration of another cell or tissue location. The propagation of ATP induced calcium elevation in the stimulated cell to other cells via gap junctions or other pathways can be evaluated. Similar methodology can be used to study diffusion of metabolic stimulators in tissues. Signal transmission can be distinguished from diffusion by its time dependence and dynamic response. The use of two probes simultaneously as the first step in the development of the perfusion probe array methods.

Figure 8:
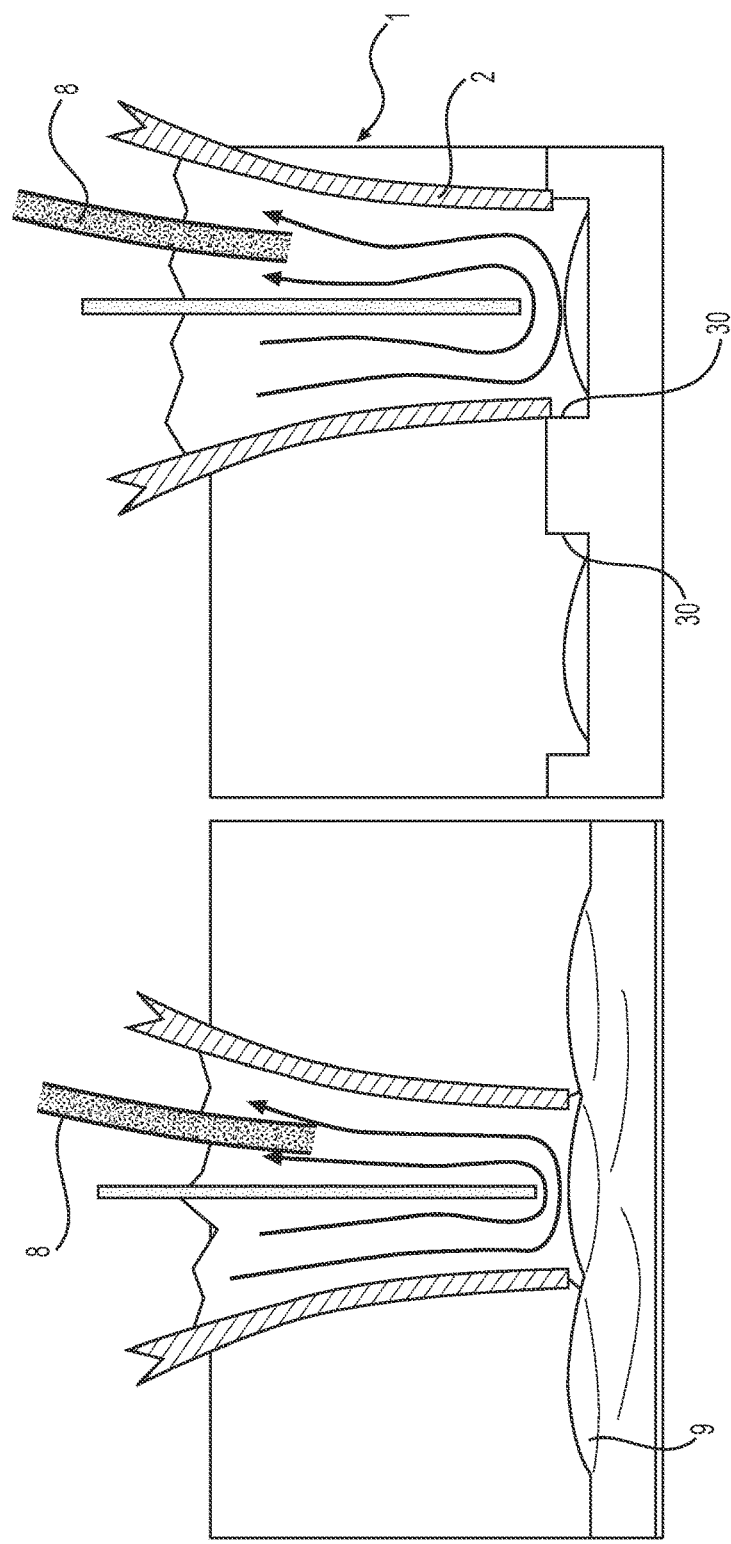
FIG. 8 is an illustration of the double-barrel pipette probe as a respirometer.

In further discussing the design of the inventive double-barrel pipette probe as a perfusion respirometer and its feasibility, reference is made to FIG. 8.

The design of the respirometer system is illustrated in FIG. 8 for applications where respiration can be highly localized to very few cells in tissues and for situations where cells are separated into micro-wells within a glass substrate. As shown in the illustration on the left side of FIG. 8, the double barrel pipette probe tip can be in contact or near contact with tissue to measure its local respiration by slowly passing fluid (cell medium) from one channel to the other. Incoming fluid is prepared with known oxygen and nutrient concentration. Oxygen, pH, ions and carbon dioxide can be measured in the outgoing fluid to characterize local tissue respiration. Various mitochondrial inducers and inhibitors can be injected into the incoming fluid. As shown in the illustration on the right side of FIG. 8, the double barrel pipette probe can be used as a respirometer in a similar way on cells separated into micro-wells (30). There is no need for hermetic covering of the cells because fluid movement (convection) dominates over diffusion.

Figure 9:
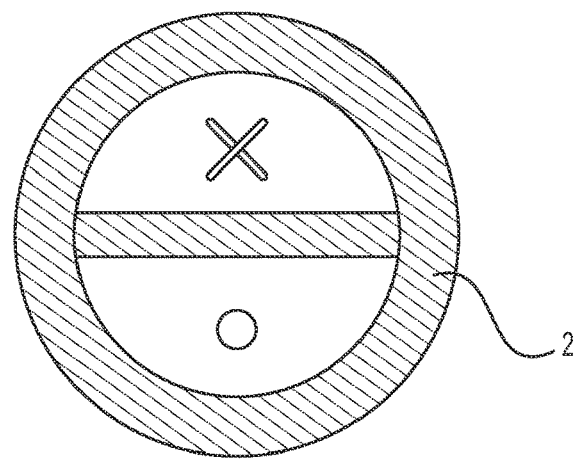
FIG. 9 shows a theta-like cross section of the typical double-barrel pipette, and the cross and dot indicate opposite flow directions.

A feature that distinguishes the inventive double barrel pipette probe used as a respirometer from previously discussed alternatives, including those for single cell analysis, is that it is based on perfusion. In other words, rather than measure oxygen consumption in a confined sealed volume, a fluid with initially known concentration of oxygen and various ions such as sodium ($Na^+$), potassium ($K^+$), chloride ($Cl^-$) as well as various nutrients constantly flows past cells, while change in oxygen concentration as well as in the concentration of ions is being measured by one or several downstream sensors. Typical cross section of the double-barrel perfusion pipette is shown in FIG. 9.

Why Perfusion is Important

Cells constantly exchange organic molecules, gasses and ions with their environment. Perfusion permits the effective exchange volume to be small at any given time, while continuing to support the flux of all required organic and inorganic species. Smaller exchange volume makes relative change of concentration of various species larger and easier to measure. In addition, perfusion permits the positioning of sensors remotely from cells circumventing possible interference with other measurement that might need to be carried out, such as various fluorescent assays, and offering greater flexibility in sensor selection or design.

In the inventive double barrel pipette probe system used as a respirometer perfusion system, the rate of fluid flow is selected to minimize back diffusion of the species to be measured. For an open flow system, this roughly implies that the mean displacement of a molecule by diffusion should be smaller than or equal to the distance of fluid displacement over the same time period. The mean square displacement by diffusion ($r^2$) is related to the diffusion coefficient D and time t by:

$$\langle r^2 \rangle = 2Dt$$

The diffusion coefficient for oxygen is around $20 \times 10^{-6}$ $cm^2/s$. Many ions actually also have similar diffusion coefficients. Therefore, in a completely open environment in 1 second these species will diffuse about $\sqrt{2D} \approx 60$ μm, necessitating flow velocity of about 60 μm/s in the pipette opening to avoid significant loss of these species. Assuming that the total pipette diameter is around 50 μm (roughly cell size), each barrel of the pipette will have about 1000 square microns in cross sectional area and the above flow speed results in the volume flow rate of about $I_f=60$ pL/s or 3.6 nL/min. This is well within the range that could be delivered by a typical syringe pump (or infusion pump), for example. However, such fluid velocity might affect some cells through sheer stress. To reduce fluid velocity near cell, while limiting back diffusion at the pipette tip, the size of the pipette opening can be reduced, while still covering the same cell area. Such modifications to the pipettes is described herein.

In a typical commercial respirometers such as Oxygraph-2K by Oroboros, good sensitivity is obtained with about $10^6$ cells/mL or, equivalently, with 1 nL/cell. Based on the above required flow rate estimates, the exchange volume will pass across a typical cell or a micro-well that would have dimensions of about 50 μm in about 1 second making the exchange volume about 60 pL, which is more than 10 times smaller than the effective exchange volume per cell within today's commercial respirometers. Since this is effectively the volume of a micro-well, reducing fluid velocity at the pipette tip, will change this exchange fluid volume.

To demonstrate the feasibility of measuring biologically relevant oxygen concentration variations using the inventive perfusion double-barrel pipette, consider typical oxygen consumption measured in about 1 mL of fluid in commercial respirometers. As shown in the example of FIG. 1, it is on the order of 10-100 pmol/(mL·s). Relevant biological changes occur typically within about 100-1000 seconds. Therefore, relevant oxygen concentration changes (measurable within minutes after introduction of some stimulus) in large cell cultures are about 0.1-1 nmol/mL. Given that the inventive double-barrel pipette probe used as a perfusion respirometer will use about 10 times less fluid per cell, the expected biologically relevant oxygen concentration change measurable within minutes should be on the order of 1-10 nmol/mL. Typical commercial fiber optic oxygen probes (for example one from Ocean Optics, PI 600 or OXB50 from Pyroscience) have detection limits lower than about 0.1-0.3 nmol/mL when signals are integrated over few seconds. Therefore, commercial oxygen sensors would provide more than sufficient sensitivity for the required measurements.

Glass capillaries of theta shaped cross section illustrated in FIG. 9 (1.5 mm outer diameter with separators in middle) can be purchased from Sutter Instrument Co. Pipette pulling will be employed to obtained pipettes having the same general shape, but dramatically reduced in size. During pipette pulling with a laser pipette puller (P-2000 from Sutter Instruments), the ends of the 1.5 mm diameter capillaries are pulled apart, while the middle of the capillary is heated by the laser. Depending on the pulling rates and the total pulling extent, the sizes of the two pipette barrels at the outlet have been varied. In the SEM images of FIG. 6, a tip diameter of 10 µm and 300 µm are shown.

Figure 10:
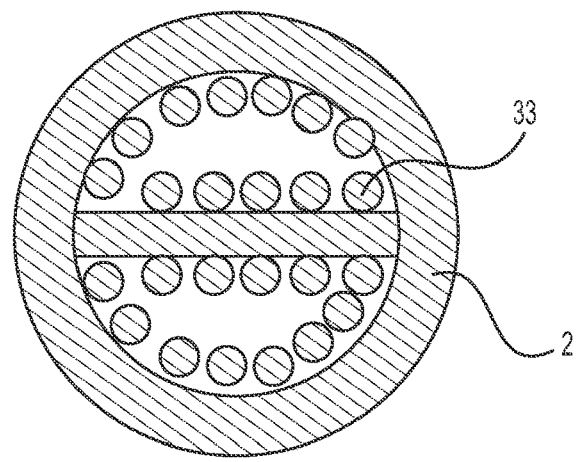
FIG. 10 shows double-barrel pipette cross section showing possible occlusion of the barrel openings to reduce back diffusion.

As discussed above, the opening of the pipette barrels can be reduced in order to limit back diffusion. This can be accomplished by a number of ways. One way is to occlude the barrel openings using deposition of material such as silica beads mixed with polymer on the barrel walls. This can be achieved by dipping the pipette tips into a solution of such material followed by drying. An illustration of the resulting cross section is shown in FIG. 10. To reduce the barrel opening area 10 times, linear dimension of the openings can be reduced about 3 times to roughly 8 µm. This will permit to reduce the flow velocity near cells from roughly 60 µm/s to about 6 µm/s. In normal tissues interstitial flow is thought to be on the order of 1 µm/s and lymph flows around the tumor margin are substantially higher.

Testing of the double-barrel pipette will be carried out using fluorescent dye, such as Rhodamine. By setting different out- and inflow rates, it will be possible to observe at which rates and, therefore, at which average flow velocities most of the dye will flow through and when diffusion of the dye would be minimized. The feasibility of such testing was demonstrated in the images shown in FIG. 11.

Numerous methods of micro-well array fabrication can be used. For instance, in the fabrication of magnetizable arrays, micro-well fabrication methods can be used based on the use of thick photoresist (SU-8) as the stamping material for fabrication of micro-well arrays in PDMS. Similar methods can be employed to stamp cell size micro-wells in PDMS and, possibly, in gels such as the agarose gel. Typical size of the micro-wells is expected to be around 50 µm×50 µm with the height around 25-40 µm.

Oxygen Sensing

Two primary methods have been employed so far to measure oxygen concentration in respirometry. One is an electrochemical method where molecular oxygen that diffuses through an oxygen permeable membrane and gets reduced (donates electron) with the help of a catalytic electrode like platinum. The other method is based on change of luminescence (fluorescence) due to proximity of oxygen. Quenching of luminescence due to proximity of oxygen can occur due to non-radiative energy transfers from the dye to the oxygen molecule and can affect both intensity and lifetime of luminescence Historically electrochemical methods were first to be used. However, miniaturization of electrochemical probes is more difficult since their structure is more complex usually requiring oxygen permeable layer. Furthermore, oxygen is consumed in the electrochemical reduction process and, for some sensors, this also modifies the electrode. Fouling affects electrochemical oxygen sensors more than the optical sensors due to the critical nature of oxygen transport through the selective membranes. For these reasons, it is preferred to use optical oxygen sensing.

Commercially available fiberoptic oxygen sensors can be used, such as OXB50 fiberoptic oxygen sensors from Pyroscience, for example, which have exposed fiber diameter of 230 µm and tips smaller than 50 µm making it possible to place the tip of the fiber in one of the pipette barrels and within about 2 mm from the opening of the pipette. In addition to investigating the use of commercially available oxygen sensors, the tip of the double barrel pipette will be used as a sensor. This can be achieved by coating the inside of the pipette barrels near the opening with fluorescent material as illustrated in FIG. 12 by a process similar to one described for occlusion of the barrel opening. The fluorescent material can be obtained in the form of fluorescent nano- or micro-beads and deposited onto the pipette walls simply by dipping the pipette tip into the fluorescent material solution and drying it subsequently. One advantage of this approach is the ability to control the area and amount of fluorescent material possibly increasing the overall sensitivity of the measurement. Another advantage is the ability to optimize the choice of the fluorescent material. Finally, this approach permits to use microscopy in direct evaluation of oxygen content in a differential fashion providing the ability to compare concentration of oxygen within the incoming and outgoing fluid flows. This, in turn, makes calibration much simpler as it permits to control for other conditions such as temperature or presence of homogenously distributed quenchers of luminescence.

Ion Sensing

While oxygen measurement has been the primary focus of respirometry, the present invention includes measurement of other analytes in the cellular environment in connection with respiration. Cells spend significant energy (ATP produced as a result of respiration), for example, on maintaining sodium/potassium ($Na^+/K^+$) pumping. Sodium is subsequently used as a co-transporter of metabolites including glucose. In many situations transport of positive ions into and out of a cell is imbalanced and chloride ($Cl^-$) is used to achieve this balance as, for example, is the case in the case of the so-called chloride shift where influx of chloride into cells is used to balance accumulation of positive carbonate ions occurring due to production of carbon dioxide. Thus, knowledge of ion fluxes across cell membranes could provide valuable biological information when correlated with consumption of oxygen.

While not employed in respiration measurement, technology for quantifying ion transport across cell membranes has been widely employed in biological studies and drug discovery (for instance, ion channels are some of the major drug targets). Patch clamps are probably the most accurate method known for measurement of ion channel currents. However, it is a highly invasive technique. Total ion flux measurements have been implemented for some time on the basis radiolabeling and more recently on the basis of fluorescent detection. Fluorescent dyes can change emission characteristics when ions bind to them. However, sensitivity can be limited during extracellular measurements. As a result, the dyes are employed mostly for intracellular measurements. However, even with fluorescent detection implementing quantification of multiple ions at the same time can be very invasive for cells. Ion selective electrodes are employed in electrochemistry, but their selectivity is often not large enough to counteract the effects of substantially different ion concentrations. Moreover, using multiple ion selective electrodes is difficult in miniature devices like single cell respirometers. Flame atomization spectroscopy has also been widely employed to study ion fluxes by characterizing changes in the extracellular ion concentration via optical emissions. The advantage of this technique is its non-invasive nature and ability to quantify multiple ions concentrations at the same time. However, until now this optical emission method required relatively large samples that could be collected from cell cultures. Nevertheless in the present invention, ion concentration measurement can be used in conjunction with the inventive double barrel pipette probe system using optical emission spectroscopy similar to flame spectroscopy. In the inventive method, emission from ions are excited with microscopic plasma discharge directly in the fluid flowing out through one of pipette barrels (channel B) away from the cell, as illustrated in FIG. 13. The required sensitivity for concentration changes of ions is on the order of 10 nmol/ml (0.05 ppm) for instruments with millions of cells per milliliter of extracellular medium. This type of sensitivity is obtained with commercially available ion flux assay instruments such as the one from Aurora Biomed Inc. ICR 8000. Reduction of the extracellular volume by a factor of 10 permits to make biologically relevant conclusions with changes of ion concentration on the order of 100 nmol/ml (0.5 ppm).

FIG. 14 summarizes and illustrates some of the results. FIG. 14 shows OES and corona discharges produced using 5 kV stepped and pulsed voltage (duration from 20 ns to several microseconds) excitation in liquids using tungsten wire with tips below 200 nm. Inset pictures a) and b) demonstrate changes can be seen as a function of the composition of the solution. Graphs c) and d) are the OES from tap water and 0.5 m NaCl, respectively. Graph e) shows the OES for 5 kV, 20 ns duration pulses in blood plasma; this spectrum does not show oxygen and hydrogen peaks and indicates that for longer discharges, light emission is due to recombined ions and decomposition of the liquid, whereas in short discharges, light emission is due solely to recombined ions. Optical micrographs indicate that the short-duration pulsed coronas (f) are less than 3 mm in diameter and are significantly smaller than discharges from microsecond-duration pulses (g), for which a larger discharge and bubble formation is seen.

Figure 15A:
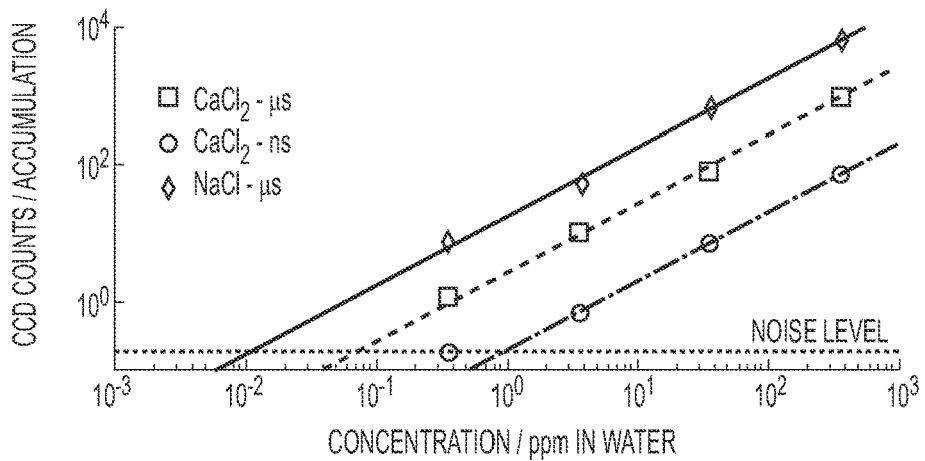
FIG. 15 shows analytical capabilities of short and long pulses of the plasma discharge.
Figure 15B:
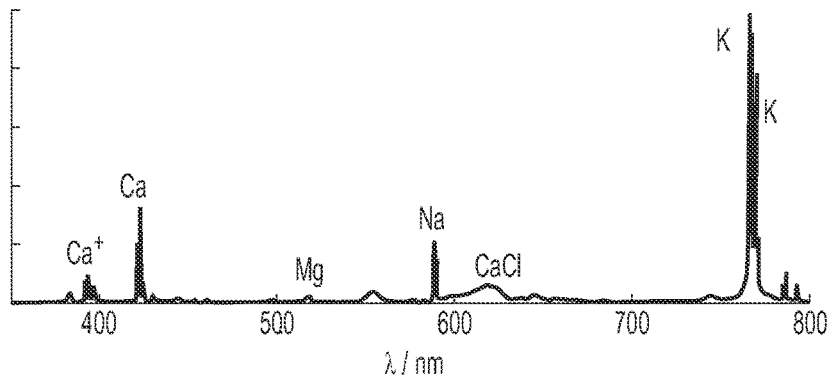

As evident from these results observation of emissions provides sufficient resolution in complex biological solutions such as blood. To study sensitivity of the micro-plasma discharge induced emissions directly from a liquid medium, the accumulated photon count data was accumulated for voltage pulses of short (down to 20 ns) and long (1 μs) durations. The results are shown in FIG. 15 per pulse. In Graph a) of FIG. 15, a single 100 ns pulse calcium ion concentration is measured to about 1 ppm concentrations in volumes smaller than 10 fL. Longer (p s) pulses can detect lower calcium concentrations down to about 0.1 ppm from volumes smaller than 20 pL. Intensity varies linearly with concentration, and a higher sensitivity is observed for sodium. Also, in Graph b) of FIG. 15, operation in a non-thermal plasma discharge regime limits the number and broadening of lines and allows multiple elements to be detected simultaneously. Using short pulses of less than 50 ns, only recombined ions are detectable. Longer pulses show both recombined ions and decomposition of the liquid. An advantage of the plasma discharge of relatively short duration creates a discharge that is much less thermal than one employed in typical flame spectroscopy. This means that the inventive probe system can include complex ions that do not atomize. Furthermore, as evident from FIG. 15, very high sensitivity can be obtained during very fast measurements. Even with a single pulse, sodium measurement is already within required limits of detection (0.5 ppm as mentioned above). Collecting the emission signal for many pulses has the potential to lower the detection limit by an order of magnitude.

In the present invention, the plasma discharge can be used within the double-barrel pipettes and calibration of its sensitivity can be performed for implementation in single cell micro-well format.

Cell Stress Evaluation under Various Device Operating Parameters

To demonstrate the applicability of the double-barrel pipette for single cell measurements, established cell lines such as human prostate cancer DU145 and PC-3, and human prostate benign PrEC with averaged respiratory activities that are known are used. For micro-array studies, the adhered cell culture are harvested and isolated cells housed in separate array wells. The double-barrel pipette probe system can be used in a tissue sample, where the complex cell-to-cell metabolic communication is preserved reflecting the "social" aspects of cell behavior, the confluent cell monolayer platform can be used as a model of tissue surface.

The fluid flow potentially can cause mechanical and biochemical stress in cells. Therefore, the flow velocity is well controlled to enable minimal mechanical force on cell surface and intracellular constituents to avoid interference of possible cellular stress responses with the measured respiratory signals. The cell health upon perfusion is examined to secure the adequate non-stressed cellular condition.

Cytosolic calcium modulations over the resting values can be diagnosed during the flow as means of cell response to mechanical perturbations. Cells loaded with calcium sensitive dye (Fluo-4 AM) can be exposed to the phosphate buffer or cell culture media streamed over the cells at variable rates. The fluorescence changes are recorded using laser confocal inverted microscope, which allows simultaneous video imaging and micro-fluorimetry. The value of fluorescence intensity of Fluo-4 measured over each tested cell are converted to the calcium concentrations. The fluid flow resulting in minimal or no cytosolic calcium elevations would be considered suitable and mechanically noninvasive.

The functional normality of cell's key metabolic organelles, mitochondria, whose undisturbed activity determines cellular homeostasis can be validated. The mitochondria membrane potential sensitive dye, TMRM, loaded into cells enables monitoring the fluctuations of mitochondria membrane potential during the flow. The perfusion should result in little or no changes in mitochondria membrane potential. At the end of each experiment, the gradually increasing doses of protonophore FCCP are injected into the perfusion stream to eliminate the mitochondria potential as means of positive control. Greater doses of FCCP applied to decrease the mitochondrial potential imply less perturbed mitochondrial energetic state and safer the perfusion condition. This methodology shows the ability of the double-barrel pipette to deliver the membrane permeable substances into a cell via perfusion flow.

The modulation of cell behavior with activators of cell surface purinergic and/or muscarinic receptors, ATP and Carbachol, respectively, can be introduced into perfusion stream. Both agents are stimulators of cell calcium homeostasis. Microscopic monitoring of dose-dependent elevation of cytosolic calcium upon activation of cell surface receptors demonstrates efficient liquid circulation through the pipette. This assay is based on fluorimetric recording and quantification of cytosolic Fluo-4 (calcium sensor) emission signal.

The double barrel pipette probes can be used as respirometers employed in an array, as illustrated in FIG. 16, to carry out single cell respiration measurements in parallel on many cells. One of the advantages of using pipettes, rather than micro-well cell chip substrates, is the ability to develop similar techniques for screening of tissues, where cell-cell interaction play a very important role. Furthermore, the technique developed here can be extended to combine carbon dioxide measurement together with oxygen and ion flux measurement. Such methods will not only contribute to biological knowledge in general, but may be suitable for tissue diagnostic tools that help physicians to find improved treatment options.

Design, Fabrication, Calibration and Control of the Inventive Double Barrel Pipette Probe as a Scanning Localized Perfusion Respirometer Probe One of the key distinguishing characteristics of living matter, its thermodynamic non-equilibrium nature, reveals itself through homeostasis of fluxes of gases, ions, and many molecules, rather than only by their instantaneous concentrations. Indeed, substantial fluxes of energy and materials are occurring through living cells even when the concentrations within them remain constant over time. Microscopic techniques are based on snap shot images of concentrations, rather than fluxes. The present invention is related to a larger vision of developing minimally invasive functional microscopy techniques for living tissues and cells that are based on localized measurement and control of fluxes.

The flux of molecular oxygen is one of the most important for living systems. Its measurement is called respirometry. It has been employed to study metabolic functions of animals, plants, tissue samples and cell cultures. Many human diseases including cancer (FIG. 2), neuromuscular degeneration and others are associated with and/or caused by metabolic dysfunctions. Given the importance of oxygen consuming metabolic activity of tissues, it is not surprising that respirometry is employed widely in biotechnology, biology and medicine.

One class of applications is in the fundamental biological study of cellular metabolism. Respiration microscopy, for example, may enable the study of functions of different mitochondrial respiratory enzymes in different locations of cells such as neurons and muscles. By employing localized perfusion capabilities, metabolic signal transmissions in 3D within tissues can be measured. The addition and substitution of different sensors, for example pH, ionic sensors, and coupling to mass spectroscopy for metabolic profiling will dramatically broaden the capabilities of the inventive method beyond respiration. Development of flux sensing arrays have applications in pathology labs where one can perform functional tissue analysis in order to reveal rare cell types and rare cell behaviors. These rare events, for example, may be associated with occurrence of metastasis, the correlation of which with differences in mitochondrial behavior has been recently confirmed. Different flux patterns following exposure to a therapeutic agent may be used by physicians to personalize therapeutic options. In principle, functional microscopy can also be performed on tissue surfaces in vivo. This may include the surfaces of skin, airways and the gastrointestinal tract enabling detection and customization of treatment of malignancies, inflammations and other diseases. Thus, not only will the present invention extend current uses of respirometry to microscopic investigations of metabolic heterogeneity in cells and tissues, it will also lay the foundations for extending the technology further to other types of useful functional microscopy.

Scanning probes of many different kinds have been used to map microscopic properties of cells and tissues. Microfluidic devices have also been built to locally perfuse cells and tissues. However, as far as the inventors know, localized perfusion has not been employed as a probe to obtain microscopic metabolic maps of tissues. The use of the double-barrel pipette probe for perfusion as illustrated in FIG. 1 is new and a key innovation of the present invention is in the kind of information that can be extracted with such a device.

The type of information that can be obtained is based on direct microscopic mapping of oxygen flux over tissue surfaces. While most scanning probe microscopy techniques measure the concentration of molecules on or above cell or tissue surfaces based on some interaction with a scanning probe, the inventive double barrel pipette probe used as a perfusion probe can directly measure oxygen flux (and by extension, other molecules and ions of interest). Although one can argue that measurements of concentrations are related to flux, this relationship is not always simple. In biology, transport of various species within cells and across cell membranes is often not driven by diffusion. Even if one assumes that the transport is diffusion dominated, flux calculation from concentration variations in space requires probe scanning in 3D. Furthermore, the signal obtained through scanning would have to be time-differentiated to yield flux information and such differentiation substantially degrades the signal-to-noise ratio. As an example, consider conventional respirometry on cell culture shown in FIG. 2 where time variation of oxygen concentration (dark line) is used to infer a noisy oxygen flux signal (grey lighter line). In contrast, the flow in the perfusion probe converts the flux of oxygen into the difference of upstream and downstream concentrations permitting direct measure of the flux without any signal differentiation or reliance on probe scanning.

Experimental

Description of Experimental Set-up for Experimental Hydrodynamic Confinement

Figure 6A:
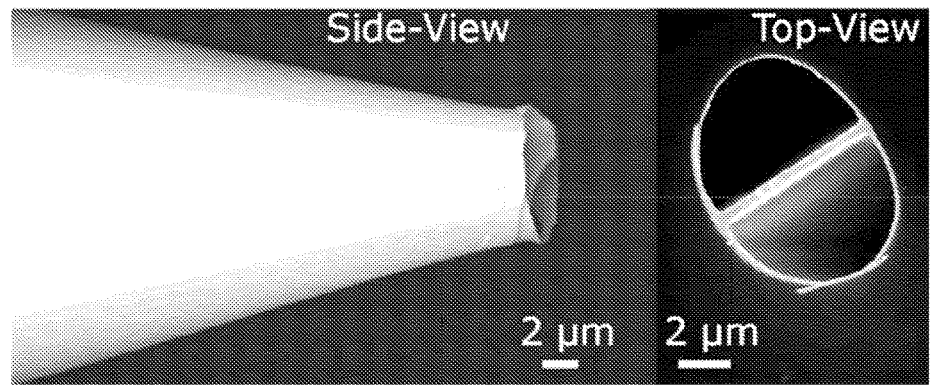
FIG. 6 shows scanning electron microscope (SEM) images of a theta pipette with tip diameter of 10 μm, side-view and top-view and SEM images of a theta pipette with tip diameter of 300 nm, side-view and top-view.
Figure 6B:
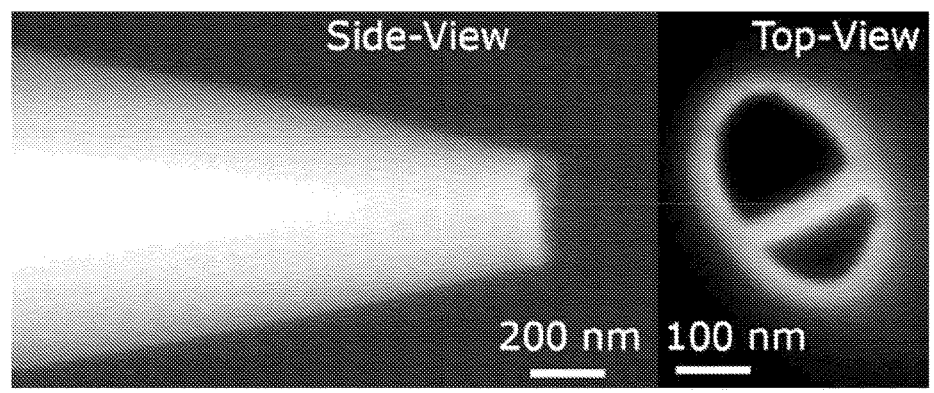

A 1.5 mm outer diameter double-barrel glass that has a theta-style cross-section (Sutter Instrument Co.) was pulled using a laser glass puller (Sutter Instrument Co., P-2000) to form dual channel micro-pipettes as shown in FIG. 6. Depending on the pulling parameters, the pipette tip diameter can be varied from 100 micrometers down to about 100 nm. The injection channel of the theta micro-pipette was loaded with saturated fluorescein (Acros Organics, Fisher Scientific; excitation/emission wavelengths 498/518 nm) aqueous solution (0.08% wt.). The extraction channel was loaded with pure water. Two plastic tubes were then inserted into the two unmodified channels at the other end of the theta capillary from the back, and sealed with epoxy (Bob Smith Ind., Quick-cure 5 mm epoxy). The injection channel was then connected to a source of positive pressure, while the extraction channel was connected to a source of negative pressure. In this work, the positive pressure was supplied by a pressure pump (Eppendorf, FemtoJet), and a syringe pump (New Era Pump Systems, Inc., Dual-NE-1000) was used to supply suction.

To study the effects of perfusion flow on molecules diffusion around the tip of the theta-style pipette, the pipette tip was immersed at a 5° angle to the substrate into a large drop of water (approximately 0.3 ml) placed on a microscope slide, while fluorescent molecules where perfused through the pipette tip. An inverted fluorescent microscope (Olympus FluoView FV1000 Confocal Laser Scanning Microscope; Sampling speed: 2.0 μs/Pixel) with a lens (LUMPLFL, 100 X W NA: 1.00) placed near the bottom of the microscope slide focused on the tip end area was employed to observe the size and intensity of the fluorescent plume. A constant withdraw speed of 5 μL/min, provided by the syringe pump, was maintained at the probe's extraction channel. Multiple experiments were performed at different injection channel pressures varying from 100 hPa to 116 hPa with of 2-3 hPa increments, and then decreased back to 100 hPa with the same step-size. The fluorescent dye plumes in the water droplet were observed and recorded.

Finite Element Model

A 3-D model was built in COMSOL Multiphysics (v4.4) to evaluate the perfusion probe's performance. Two different stationary models were involved and coupled in this model, one solved the Navier-Stokes equations (Equation (2)) for flow parameters inside the computational region:

$$\rho(\vec{v} \cdot \nabla)\vec{v} = \nabla \cdot [-p\vec{I} + \mu(\nabla \vec{v} + (\nabla \vec{v})^T)] + \vec{F} \qquad (2a)$$

$$\rho \nabla \cdot \vec{v} = 0 \qquad (2b)$$

where $\rho$ is the density, $\vec{v}$ is the calculated flow velocity field, $p$ is the pressure, $\vec{I}$ is the unit vector, $\mu$ is the dynamic viscosity, and $\vec{F}$ is the volume force field, respectively.

Another study solved the convection diffusion equations (Equation (3)) for concentration distribution:

$$\nabla \cdot (-D\nabla c) + \nabla \cdot (\vec{v} c) = R \qquad (3a)$$

$$\vec{N} = -D\nabla c + \vec{v} c \qquad (3b)$$

where
e D is the diffusion coefficient, c is the species mass concentration, $\vec{v}$ is the flow velocity field calculated from the previous study, R is the reaction rate, and $\vec{N}$ is the flux, respectively.

For hydrodynamic confinement verification, a 400 μm quartz theta pipette was built at the top center in a rectangular computational region of (500×400×400 μm$^3$). The theta pipette had a tip diameter of 20 μm, and its outer wall was formed by a truncated cone with half-angle of 8.5°. Its separation was formed by a rectangle frustum, used in simulation to achieve similar pipette tip geometry from the experimental images. All the walls of this geometry were defined as no slip walls. A negative pressure and a positive pressure was defined respectively on the top boundaries of the two channels to form the injecting and extracting flow in the laminar flow module. The calculated flow field was then used as the flow parameters in the convection and diffusion study. Under the experimental conditions, diffusion was tested to have practically no effect on the flow. To set up the flow condition, at one channel of this pipette, a constant negative pressure of −120 hPa was provided to supply suction. At the other channel, positive pressure was supplied from 100 to 117 hPa at several steps increments. The upper boundary of the model is set to open boundary. These flow parameters were set to match experimental conditions. For convection and diffusion studies, the initial species concentration of the whole computational area was set to zero and the inflow concentration was set to 2407 μM (fluorescein saturated aqueous solution). The diffusion coefficient was set to 0.425×10$^{-5}$ cm$^2$/s (fluorescein diffusion coefficient in water at room temperature). No cells or consumers were included in this model.

Similar model parameters were used to evaluate the probe for cell oxygen consumption sensing with modifications based on the different experimental setup, such as introducing the cell and the substrate to the model. To be specific, the rectangular computational region was reduced to (410×300×300 μm$^3$) and the substrate was placed 10 μm from the theta pipette tip. The tip diameter of pipette was set to 12 μm to have a high spatial resolution necessary for single cell studies. An ellipsoid with 5 μm, 5 μm, and 2.5 μm as it's a, b, c axis was attached to bottom of the calculation area and used to represent cell. This ellipsoid was defined as an oxygen reactor with reaction rate=0.04 mol/m$^3$·s, which resulted in a total oxygen consumption rate of 10$^{-17}$ mol/s. The boundaries of the reactor are set to be slip so that the flow velocity will not be artificially set to zero. Simulations were run for tip-substrate distances varying from 5.2 μm to 16 μm. A negative pressure and an equal value positive pressure were defined respectively on the top boundaries of the two channels to form the injecting and extracting flow. The upper boundary of the model was set as open boundary. For convection and diffusion studies, the injection boundary concentration was set to 250 μM (saturated oxygen concentration in water at room temperature). A symmetric boundary condition of 250 μM was set to the extraction boundary, as well as the upper boundary of the computational region. The diffusion coefficient of oxygen was set to 2×10$^{-5}$ cm$^2$/s (oxygen in water at room temperature). The oxygen concentration difference was recorded inside the extraction channel of the theta pipette at 150 μm above the tip. A tetrahedral mesh with maximum mesh size of 14.4 μm, minimum mesh size of 0.615 μm, maximum element growth rate of 1.35, curvature factor of 0.3, resolution of narrow regions of 0.85 was used to divide the system for FEM calculation. It was verified that meshes and the computational region size used here are appropriated for solving. Compared to a finer mesh setting, the calculated concentration differences are less than 5%, and compared to a wider computational region setting of 410×320×320 μm$^3$, the calculated concentration differences are less than 1%. Directed solvers are selected in all studies to have the most accurate result with relative tolerance set to 10$^{-6}$.

CONCLUSIONS

An aspect of the invention is a perfusion double-barrel micro-pipette as a microfluidic system that is important and useful for investigating metabolic variations among individual cells associated with changes in biological functions and disease development.

The use of FEM to study the behavior of this microfluidic system not only verifies experimental results demonstrating the feasibility of the inventive approach, but also allows to obtain theoretical insights into pipette performance/sensitivity that would require extensive studies, if done experimentally. In particular, the effects of the micro-pipette operation parameters on the system oxygen sensing capacity were considered first. It was found that the mere presence of the pipette over the cell increases the oxygen concentration difference that can be sensed; also, the use of the micropipette increases the overall sensitivity of the probe as the sensor is moved away from the pipette tip, due to oxygen confinement. In addition, the larger diameter of the pipette channel far from the tip allows the use of sensors with larger surface area. When the sensor is placed far from the tip end, introducing an appropriate perfusion flow to the system can not only maintain a constant cell micro-environment, but also further confine the free diffusion, amplifying the signal (oxygen concentration difference) at the sensor location and preventing back diffusion. It was shown that micro-scale tips, could be used to cover an average cell area, maximizing the signal intensity, and that, pipettes with sub-micro tips could be produced to obtain spatial resolution at subcellular levels, see FIG. 6. It is also worth mentioning that the developed probe is certainly not limited to oxygen measurement. By using different sensors, including electrochemical or optical ones, other types of analyses can be carried out over the surface of living tissue. Applications of the inventive system could be made in analytical chemistry or forensic study for spatially resolved microanalysis.

It is to be understood, however, that even though numerous characteristics and advantages of the present invention have been set forth in the foregoing description, together with details of the method, composition and function of the invention, the disclosure is illustrative only, and changes may be made in detail, within the principles of the invention to the full extent indicated by the broad general meaning of the terms in which the appended claims are expressed.

KEY TO DRAWINGS (1) Double barrel pipette probe
(2) Pipette shaft body
(3) Separator wall
(4) Inner wall of the pipette shaft body
(5) Distal end of tip
(6) Channel A
(7) Channel B
(8) Oxygen sensor
(9) Tissue sample
(20) Capillary tube
(21) Fluid pump
(22) Motorized computer controlled stage
(23) Component for measuring pressure of fluid
(24) Tissue sample held in place by suction
(25) Infusion pump
(30) Well for isolating cell
(33) Occluding material
(41) Coating
(42) Microscope objective
(43) Substrate for holding the single cell or tissue
(50) Plasma discharge wire
(51) Plasma discharge
(52) Fiber optic wire
(53) Spectrum analyzer
(60) Array of more than 2 double barrel pipette probes
(61) Array of wells

What is claimed is:

1. A method of perfusing a single cell with a liquid and measuring the single cell's effect on the liquid using a double barrel pipette probe (1) comprising a pipette shaft body (2) having a distal end (5), wherein the pipette shaft body (2) comprises a channel A (6) and a channel B (7)), wherein channel A (6) is configured for guiding a liquid out of the distal end (5) of the pipette shaft body (2) and channel B (7) is configured to receive the liquid exiting channel A (6) at the distal end (5) of the pipette shaft body (2), wherein said channel B (7) comprises or is in fluid connection with a sensor module for measuring concentration of material in the liquid or a temperature of the liquid,
    said method comprising steps of:
    positioning said distal end (5) of the pipette shaft body (2) in proximity to said single cell,
    flowing the liquid having a baseline concentration of material or baseline temperature from channel A (6) to channel B (7) at the distal end (5) of pipette shaft body (2) while perfusing said single cell with the liquid exiting channel A (6),
    measuring the concentration of the material in the liquid or the temperature of the liquid with the sensor module in channel B (7), and
    comparing the baseline concentration of material or baseline temperature with the concentration of material or the temperature of the liquid as measured by the sensor module to determine an effect of said single cell on the concentration or temperature value.

2. The method according to claim 1, wherein a separator wall (3) connects opposite sides of an inner wall (4) of the pipette shaft body (2) and said separator wall (3) is formed in a plane bisecting a lumen of the pipette shaft body (2) in a longitudinal direction, said separator wall (3) separates the pipette shaft body (2) into said two channels A (6) and B (7) in a manner whereby channel A (6) is parallel to channel B (7) and, in said method, a direction of flow of liquid within channel A (6) is opposite a direction of flow of liquid within channel B (7).

3. The method according to claim 1, wherein the pipette shaft body (2) has a conical tip portion narrowing at the distal end (5) of the pipette shaft body (2) and the distal end (5) of the pipette shaft body (2) has a diameter of from about 100 nm to about 100 microns.

4. The method according to claim 1, wherein the single cell is one cell in a tissue sample (9) containing other cells.

5. The method according to claim 4, wherein the double barrel pipette probe (1) is a first pipette probe and said method further comprises a step of perfusing a second single cell with a liquid using a second double barrel pipette probe located in proximity to a second single cell in the tissue sample, determining a baseline concentration of a material in the liquid in channel B of the second pipette probe, adding a modulator to the liquid in channel A of the first pipette probe, and measuring for variations of said concentration of the material in the liquid in channel B of the second pipette probe.

6. The method according to claim 4, wherein a single cell on the surface of the tissue is exposed to a modulator at a baseline concentration and/or for a duration and the depth of response within the tissue cells is measured, subsequently the single cell on the surface of the tissue is exposed to a modulator at an increased concentration and/or for an increased duration and the depth of response within the tissue cells is measured.

7. The method according to claim 1, wherein the material comprises oxygen and the liquid further comprises a respiration modulator.

8. The method according to claim 7, wherein the respiration modulator is at least one selected from the group consisting of a metabolite, a mitochondrial electron transport inhibitor, a chemotherapeutic agent, and a compound which affects extracellular pH.

9. The method according to claim 1, wherein the material is at least one of oxygen, an alkali metal cation, an alkaline earth metal cation and a halide.

10. The method according to claim 1, wherein the flow of liquid from channel A (6) to channel B (7) is maintained for at least 10 minutes.

11. The method according to claim 1, wherein the cell is an animal cell.

12. The method according to claim 1, wherein a wall of channel B (7) and a wall of channel A (6) have a carbon coating.

13. The method according to claim 1, wherein the sensor module is a coating (41) capable of providing a fluorescent response in the presence of at least one of glucose, lactose, protein, carbon dioxide, sodium, chlorine, potassium, iron, magnesium and calcium.

14. The method according to claim 13, wherein a microscope objective (42) is positioned below a substrate (43)

holding the single cell or tissue containing the single cell so as to receive a light signal through the substrate.

15. The method according to claim 1, wherein the sensor module is an oxygen sensor (8) or a plasma discharge wire (50).

16. The method according to claim 1, wherein channel A (6) comprises a sensor module.

\* \* \* \* \*